United States Patent
Nuopponen et al.

(10) Patent No.: US 11,723,867 B2
(45) Date of Patent: Aug. 15, 2023

(54) METHOD FOR PREPARING PHARMACEUTICAL COMPOSITION AND PHARMACEUTICAL COMPOSITION

(71) Applicant: UPM-Kymmene Corporation, Helsinki (FI)

(72) Inventors: Markus Nuopponen, Helsinki (FI); Huang Xiang, Changshu (CN); Haiqiu Song, Suzhou (CN); Yulong Wang, Changsha (CN); Yanxin Liu, Changsha (CN)

(73) Assignee: UPM_KYMMENE CORPORATION, Helsinki (FI)

( * ) Notice: Subject to any disclaimer, the term of this patent is extended or adjusted under 35 U.S.C. 154(b) by 289 days.

(21) Appl. No.: 17/015,298

(22) Filed: Sep. 9, 2020

(65) Prior Publication Data

US 2021/0077403 A1    Mar. 18, 2021

(30) Foreign Application Priority Data

Sep. 13, 2019  (EP) .................................... 19397527

(51) Int. Cl.
  *A61K 9/14*    (2006.01)
  *A61K 9/16*    (2006.01)
  *A61K 31/7048*    (2006.01)

(52) U.S. Cl.
  CPC .......... *A61K 9/1652* (2013.01); *A61K 9/1694* (2013.01); *A61K 31/7048* (2013.01)

(58) Field of Classification Search
  None
  See application file for complete search history.

(56) References Cited

U.S. PATENT DOCUMENTS

| | | | |
|---|---|---|---|
| 6,361,797 B1 | 3/2002 | Kuzma et al. | |
| 2012/0135081 A1 | 5/2012 | Laaksonen et al. | |
| 2013/0330379 A1 | 12/2013 | Ylipertula et al. | |
| 2014/0322327 A1* | 10/2014 | Laukkanen | A61K 31/216 514/420 |
| 2015/0367024 A1 | 12/2015 | Laukkanen et al. | |
| 2016/0325008 A1* | 11/2016 | Laukkanen | A61L 27/3834 |
| 2019/0083626 A1 | 3/2019 | Golodberg et al. | |
| 2021/0085602 A1 | 3/2021 | Nuopponen et al. | |

FOREIGN PATENT DOCUMENTS

| | | |
|---|---|---|
| CN | 103520739 A | 1/2014 |
| JP | H10248872 A | 9/1998 |
| WO | 2013072563 A1 | 5/2013 |

OTHER PUBLICATIONS

Paukkonen, H. et al. "Nanofibrillar cellulose hydrogels and reconstructed hydrogels as matrices for controlled drug release", International Journal of Pharmaceutics, vol. 532, 2017; 12 pages.
Bhadari, J. et al., "Cellulose nanofiber aerogel as a promising biomaterial for customized oral drug delivery", International Journal of Nanomedicine, vol. 12; 2017; pp. 2021-2031.
Jackson, J. K. et al., "The use of nanocrystalline cellulose for the binding and controlled release of drugs", International Journal of Nanomedicine, vol. 6, 2011; pp. 321-330.
Valo, H. et al., "Immobilization of protein-coated drug nanoparticles in nanofibrillar cellulose matrices—Enhanced stability and release", Journal of Controlled Release, vol. 156, 2011; pp. 390-397.
Graves et al., "In Vitro Dissolution Method for Evaluation of Buprenorphine In Situ Gel Formulation: A Technical Note," AAPS PharmSciTech, vol. 8, No. 3, 2007, Article 62; 4 pages.

* cited by examiner

*Primary Examiner* — Susan T Tran
(74) *Attorney, Agent, or Firm* — Cantor Colburn LLP

(57) ABSTRACT

The present application relates to a method for preparing a pharmaceutical composition, the method comprising providing pharmaceutical compound having a solubility in water of 1 mg/ml or less at 25° C. in a solvent enabling solubilizing the pharmaceutical compound at least partly into the solvent, providing an aqueous dispersion of nanostructured cellulose, and combining the pharmaceutical compound with the aqueous dispersion of nanostructured cellulose in an anti-solvent process to provide nanosized pharmaceutical particles having an average diameter of 50 nm or less, to provide a pharmaceutical composition. The present application also provides pharmaceutical composition, and use of the pharmaceutical composition.

17 Claims, 13 Drawing Sheets

US 11,723,867 B2

METHOD FOR PREPARING PHARMACEUTICAL COMPOSITION AND PHARMACEUTICAL COMPOSITION

CROSS REFERENCE TO RELATED APPLICATION

This application claims the benefit of European Application No. 19397527.3 filed on Sep. 13, 2019, which is incorporated by reference herein in its entirety.

TECHNICAL FIELD

The present application relates to a method for preparing a pharmaceutical composition, and to a pharmaceutical composition. The present application also provides a method for stabilizing a pharmaceutical compound having a low solubility in water.

BACKGROUND

At present, water-insoluble drugs account for about 40% in the drug market on sale. The water-insolubility of drugs causes a series of problems in a body, such as low bioavailability, excessive drug use, and waste of drugs. It is desired to improve the dissolution and bioavailability of such drugs.

SUMMARY

It was found out how to improve the dissolution and bioavailability of poorly water-soluble pharmaceuticals. When nanostructured cellulose was used as a matrix for the pharmaceutical compound, it could stabilize the compound and prevent the precipitation of the compound, so that the compound remained in a dispersion. Using the dispersion prevented or greatly reduced agglomeration, aggregation, clotting and/or mounting by gravity of the pharmaceuticals. The dissolution rate of the pharmaceutical compound was increased, which can enhance the delivery of the compound into a target.

This enables providing pharmaceutical compositions of a variety of types for a variety of uses, such as oral, topical or injectable compositions.

The present application provides a method for preparing a pharmaceutical composition, the method comprising
  providing pharmaceutical compound having a solubility in water of 1 mg/ml or less at 25° C. in a solvent enabling solubilizing the pharmaceutical compound at least partly into the solvent,
  providing an aqueous dispersion of nanostructured cellulose, and
  combining the pharmaceutical compound with the aqueous dispersion of nanostructured cellulose in an anti-solvent process to provide nanosized pharmaceutical particles having an average diameter of 50 nm or less, to provide a pharmaceutical composition, preferably having a water content in the range of 92-99.95% (w/w).

The present application also provides a method for stabilizing a pharmaceutical compound having a low solubility in water.

The present application also provides a pharmaceutical composition comprising nanosized pharmaceutical particles of a pharmaceutical compound having a solubility in water of 1 mg/ml or less at 25° C., the nanosized pharmaceutical particles having an average diameter of 50 nm or less, in a nanostructured cellulose matrix, the pharmaceutical composition preferably having a water content in the range of 92-99.95% (w/w).

The present application also provides the pharmaceutical composition for use as a medicament, preferably for stabilizing a pharmaceutical compound having a solubility in water of 1 mg/ml or less at 25° C.

The present application also provides the pharmaceutical composition for use as a medicament, preferably for enhancing bioavailability of a pharmaceutical compound having a solubility in water of 1 mg/ml or less at 25° C.

The present application also provides use of nanostructured cellulose for stabilizing a pharmaceutical compound having a low solubility in water.

The present application also provides use of nanostructured cellulose for enhancing bioavailability of a pharmaceutical compound having a low solubility in water.

The main embodiments are characterized in the independent claims. Various embodiments are disclosed in the dependent claims. The embodiments and examples recited in the claims and the specification are mutually freely combinable unless otherwise explicitly stated.

Without binding to any specific theory, the inventors believe that the large specific surface area and the network structure of the nanostructures cellulose will provide more sites for poorly soluble drug compound nuclei, which will prevent the drug compound particles from overgrowing and make the drug compound nanoparticles more stable in the aqueous solution. The interactions between the drug compounds could be electrostatic adsorption and hydrogen bonding. The preparation process facilitated nanonization and dispersing of the nanonized drug particles, which were initially present as larger particles, into a number of smaller nanoparticles and maintaining them in such form, which could be considered as nanocomposite form.

The nanostructured cellulose used in the embodiments also provides hydroxyl radical scavenging activity, which helps protecting the pharmaceutical compounds and maintaining them in stable and active form.

It is therefore possible to obtain drug formulations which provide better stability, bioavailability and dissolution rate of the drug. New kind of drug formulations can be prepared, which may use new administration routes, doses and regimes.

The obtained pharmaceutical compositions could have a very high water content, up to 99.95%, which enables providing a variety of different kind of pharmaceutical formulations for poorly water-soluble compounds.

DETAILED DESCRIPTION

Figure 1:
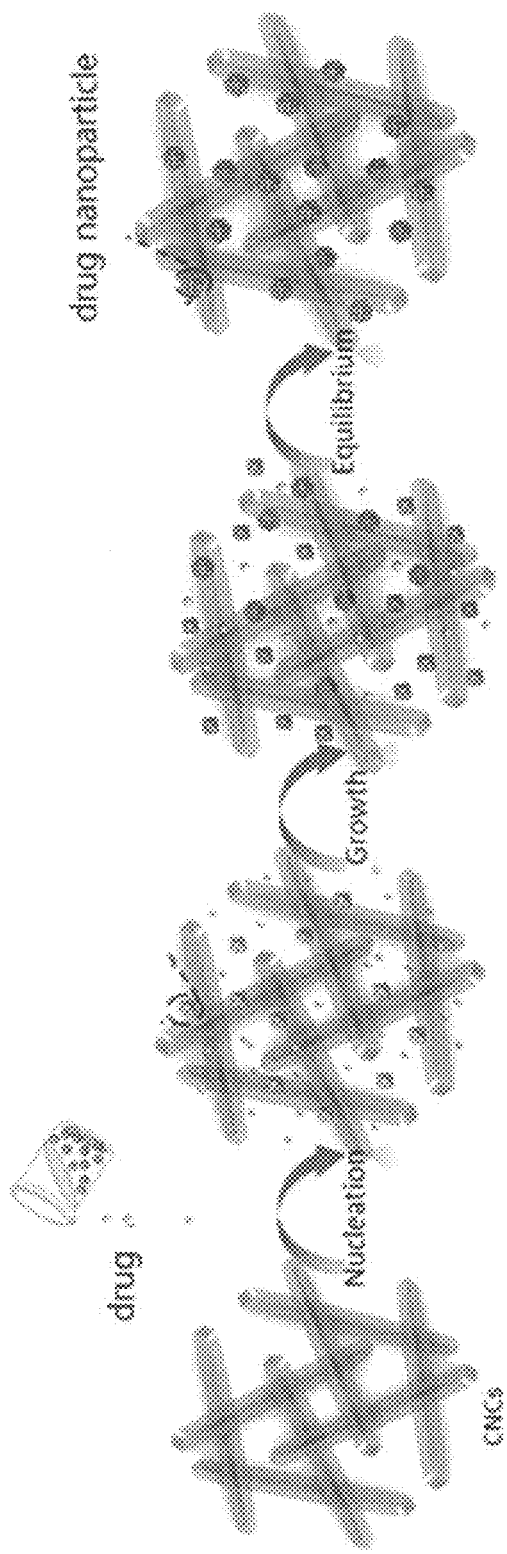
FIG. 1 shows a schematic illustration of the formation of CNC/drug nanocomposites by anti-solvent recrystalization process

In this specification, percentage values, unless specifically indicated otherwise, are based on weight (w/w). If any numerical ranges are provided, the ranges include also the upper and lower values. The open term "comprise" also includes a closed term "consisting of" as one option.

One of the major problems associated with poorly soluble drugs is very low bioavailability, Poorly water soluble drugs often require high doses in order to reach therapeutic plasma concentrations. It is not always possible to use oil-based carriers either. For example there are some compounds that are poorly soluble also in oils because of a high melting point so they do not apply so well for lipid-based delivery.

There is often drug supersaturation generated in the intestinal lumen, which may evolve in the course of formulation dispersion and digestion. This may lead to drug precipitation. Once a pharmaceutical compound precipitates in crystalline form, it will usually result in incomplete absorption.

Solubility of drug product can be defined as both quantitatively and qualitatively. Quantitative solubility is defined as that milligram of solute particles required to make a saturated solution. Qualitative solubility is defined as where two phases are mixed together to form a homogenous solution.

The introduction of new method, such as combinatorial chemistry and high throughput screening, the newly developed active agents may have a higher molecular weight and increased lipophilicity, which results in decrease in aqueous solubility of the active agent.

There are some examples where an active compound exhibit low solubility, such as when an active compound has five or more than five carbon atoms, value of log P is two or greater than two, or when molecular weight of the compound is greater than 500 Daltons. These above mentioned examples are referred to as Lipinski rule, which demonstrate active compound as non-aqueous or poorly aqueous soluble Compounds with solubilities below 1 mg/ml face significant obstacles, and often even those falling below 10 mg/ml present formulation difficulties related to solubilisation. Those compounds with poor water solubility that do get through to the market are frequently prone to suboptimal performance owing to low levels of absorption, and the effects of food intake when delivered orally.

A biopharmaceutics drug classification may be based on recognizing drug dissolution and gastrointestinal permeability as the fundamental parameters controlling rate and extent of drug absorption.

United States Pharmacopeia (USP 23) and BP classify the solubility regardless of the solvent used, just only in terms of quantification

TABLE 1

USP and BP solubility criteria.

| Descriptive term | Part of solvent required per part of solute | g/l in water |
| --- | --- | --- |
| Very soluble | Less than 1 | more than 1000 |
| Freely soluble | From 1 to 10 | 1000 to 100 |
| Soluble | From 10 to 30 | 100 to 33 |
| Sparingly soluble | From 30 to 100 | 33 to 10 |
| Slightly soluble | From 100 to 1000 | 10 to 1 |
| Very slightly soluble | From 1000 to 10,000 | 1 to 0.1 |
| Practically insoluble | 10,000 and over | less than 0.1 |

The pharmaceutical compounds suitable for the present methods and compositions may be classified as very slightly soluble and/or practically insoluble, such as requiring at least 1000 parts of solvent per part of solute (the pharmaceutical compound), for example at least 5000 parts of solvent per part of solute or at least 10000 parts of solvent per part of solute. Also slightly soluble compounds may be applied.

Another classification is Biopharmaceutics Classification System (BCS), wherein drugs are classified as BCS-I to BCS-IV. The BCS is a scientific framework for classifying a drug substance based on solubility, permeability, and dissolution criteria. According to the BCS, drug substances are classified as follows:

Class I: High permeability and solubility
Class II: High permeability and low solubility
Class III: Low permeability and high solubility
Class IV: Low permeability and low solubility.

The pharmaceutical compounds suitable for the present methods and compositions may be classified as Class IV compounds with BCS classification, optionally also Class II compounds. In general it has been considered very challenging task to improve parameters for drugs belonging to BCS-IV.

For classification purposes, American regulatory body Food and Drug Administration (FDA) considers a highly soluble drug when the highest dose strength is soluble in <250 ml of water over a pH range of 1 to 7.5. A drug substance is considered highly permeable by FDA when the extent of absorption in humans is determined to be >90% of an administered dose, based on mass-balance or in comparison to an intravenous reference dose It was found out that by using nanostructured cellulose as a matrix, vehicle and/or carrier material, specific nanocomposite structures with pharmaceutical compounds could be formed, preferably nanocomposites comprising pharmaceutical compound in nanoparticulate form in nanostructured cellulose matrix. These nanocomposites could increase the dissolution rate and bioavailability of the pharmaceutical compounds, even if originally poorly water soluble and/or poorly bioavailable compound was used. The dissolution rate could be 50% faster compared to corresponding uncompounded drug particle, even 90% faster, at 10 minutes. It was shown that the dissolution rate could be at least 50%, at least 70%, at least 80% or at least 85% at 10 minutes, and at least 90%, at least 95% or even at least 99% at 120 minutes. Compared to matrix with uncompounded drug the dissolution rate was 50% faster or higher, even 90% faster or higher. In one embodiment the pharmaceutical compound has a dissolution rate from the nanostructured cellulose matrix of 50% or more in 10 minutes, such as in the range of 50-90% in 10 minutes The present application provides methods and compositions for stabilizing a pharmaceutical compound, or for enhancing bioavailability of a pharmaceutical compound. More particularly the present application provides a method for stabilizing a pharmaceutical compound having a low solubility in water, preferably of 1 mg/ml or less, the method comprising preparing a pharmaceutical composition with the method described herein to stabilize the pharmaceutical compound.

The present application also provides a method for enhancing bioavailability of a pharmaceutical compound having a low solubility in water, preferably of 1 mg/ml or less, the method comprising preparing a pharmaceutical composition with the method described herein.

The present application also provides use of nanostructured cellulose for stabilizing a pharmaceutical compound. The present application also provides use of nanostructured cellulose for enhancing bioavailability of a pharmaceutical compound.

The present application provides a method for preparing a pharmaceutical composition or a pharmaceutical product, the method comprising
  providing pharmaceutical compound having a solubility in water of 1 mg/ml or less at 25° C. in a solvent enabling solubilizing the pharmaceutical compound at least partly into the solvent,
  providing an aqueous dispersion of nanostructured cellulose, and
  combining the pharmaceutical compound with the aqueous dispersion of nanostructured cellulose in an antisolvent process to provide nanosized pharmaceutical particles having an average diameter of 50 nm or less, to provide a pharmaceutical composition.

The present application also provides a pharmaceutical composition or a pharmaceutical product obtained with said method. A pharmaceutical product is an isolated product, which may be provided as a ready for use, such as packed, incorporated in a carrier or a vehicle and/or otherwise prepared to be used. Intermediate products of a process are excluded from the definition.

The product may be in a form having a water content in the range of 92-99.95% (w/w), which is a very high water content, so the obtained composition or product is suitable for different types of administrations. The composition may be present as a flowing dispersion, but it may be also present a hydrogel. In one example the dispersion of nanostructured cellulose comprises hydrogel.

For example injectable compositions may have a water content in the range of 92-99.95% (w/w) and/or content of nanostructured cellulose in the range of 0.05-8% (w/w). The content of nanostructured cellulose may be in the range of 1-8% (w/w), such as 1-7% (w/w) or 1-6% (w/w), especially when it is desired that the composition is in a form of a hydrogel.

In specific embodiments, wherein the nanostructured cellulose is provided mainly as a dispersant, the content of nanostructured cellulose may be in the range of 0.05-0.5% (w/w), such as in the range of 0.05-0.4% (w/w) or 0.1-0.5% (w/w) which does not form a gel. In these cases the water content may be in the range of 99.4-99.95% (w/w), such as 99.5-99.95% (w/w). The content of the nanostructured cellulose may also be in the range of 0.05-1.4% (w/w), 0.1-1.4% (w/w), 0.05-3% (w/w), 0.1-3% (w/w), 0.5-3% (w/w) or 1-5% (w/w), for example. A suitable concentration may be selected according to the intended use. The composition may contain nanostructured cellulose as the only polymeric material in the composition, and the composition may contain substantially only or consist of the pharmaceutical compound(s), the nanostructured cellulose and water. In some cases minor amounts of additives customary in the art, such as colouring agent(s), preservative agent(s) or the like agents, which preferably have no effect to the structure of the composition, may be included, preferably in an amount of 0.5% (w/w) or less, such as 0.2% (w/w) or less, or 0.1% (w/w) or less.

The water content may be calculated or adjusted accordingly, for example by summing up the percentages of nanofibrillar cellulose and pharmaceutical component, and possibly any additives, wherein the rest may be water.

The pharmaceutical compound may have a low solubility in water and/or low bioavailability. The low solubility may refer to any of the low solubilities disclosed herein, such as a solubility of 1 mg/ml or less, 0.6 mg/ml or less, or 0.3 mg/ml or less at 25° C. The pharmaceutical compound may have a solubility of 0.1 mg/ml or less in water at 25° C., which means very low solubility causing problems in most applications involving aqueous environment. The solubility may be even lower, such as 0.05 mg/ml or less, or 0.02 mg/ml or less, at 25° C. for very poorly soluble compounds. The solubility may be determined by using any suitable method or standard, such as USP 25, which is a rotating disc method. In many cases the solubility of a compound is determined computationally, such as by using a ALOGPS software (for example ALOGPS 2.1).

Examples of poorly water-soluble pharmaceutical compounds include naringenin having a solubility in water of 0.214 mg/ml (ALOGPS), azithromycin having a solubility in water of 0.514 mg/ml at 25° C. (BCS-II, ALOGPS), repaglinide which is an example of Zwitterion drug with poor water solubility of 37 mg/l, atazanavir which as a free base is practically insoluble in water (<1 mg/l) and has shown poor oral bioavailability in preclinical animal models. Further, carprofen has very low solubility in water of 0.00379 mg/ml (3.79 µg/ml), as well as itraconazole which has a solubility of 1 µg/l (0.001 µg/ml) at neutral pH. Other examples of poorly water soluble and/or poorly bioavailable drugs include carbamazepine, gabapentinin, modafinil, piroxicam, caffeine, camptothecin, vinpocetine, fenofibrate, Tacrolimus, Lopinavir/Ritonavir, Nabilone, Nimodipine, Fenofibrate, Etravirine, porphyrins, minoxidil, peptides and anthracyclines, Cyclosporine A, Diazepam, Dexamethazone palmitate, Etomidate, Flurbiprofen, Prostaglandin-E1, Propofol, perflurodecalin and perflurotripropylamine, Vitamins A, D, E and K, oral products which yield an emulsion or microemulsion in the gastrointestinal tract such as cyclosporin, Calcitrol, Clofazimine, Doxercalciferol, Dronabionol, Dutasteride, Isotretinoin, Ritonavir, Paricalcitol, Progesterone, Saquinavir, Sirolimus, Tritionoin, Tipranavir, Valproic acid, and cancer drugs, such as pactitaxel.

One or more of the above, and/or other pharmaceutical compound(s) may be included in the pharmaceutical compositions described herein. The pharmaceutical compound may or may not comprise one or more of anti-tumor, anti-cancer, anti-bacterial, such as antibiotic, anti-viral, anti-inflammatory, anti-allergic and analgesic (painkiller) agent(s), such as an opioid or a nonsteroidal anti-inflammatory drug, and/or other agent(s) disclosed herein. In one example the pharmaceutical compound is not an analgesic compound, especially when the pharmaceutical composition is in an injectable form. The pharmaceutical compound may be a medicament, i.e. a drug compound, but the term may also include other applicable bioactive substances or agents, such as plant-derived bioactive agents, for example flavonoids and the like.

Nanostructured cellulose, such as nanocrystalline cellulose or nanofibrillar cellulose, may be used for forming nanocomposite structures with a pharmaceutical compound by using anti-solvent recrystallization process, as schematically shown in FIG. 1.

The pharmaceutical compound, which may be poorly water soluble as discussed herein, may be initially provided in powder form or in the form of particles, such as in a dry form. The pharmaceutical compound may be also provided in a solution or a dispersion or the dry form may be formed into a solution or a dispersion, preferably with a suitable solvent, which may contain water or which may be other than water, such as an organic solvent, or aqueous solution, dispersion or emulsion containing organic solvent. The solvent may enable solubilizing the pharmaceutical compound at least partly into the solvent. The pharmaceutical compound may be provided to the method in the solvent. Examples of organic solvents include methanol, ethanol, 1-propanol, 2-propanol, 1-butanol, 1-octanol, propylene glycol, toluene, acetone, 1,4.dioxane, ethyl acetate, isopropyl myristate, acetonitrile, chloroform, n-hexane, cyclohexane, dimethyl sulfoxide (DMSO), N-methyl-2-pyrrolidone (NMP), dimethyl formamide (DFM) and mixtures thereof. The solvent may be for example ethanol, such as anhydrous ethanol. The solvent may be selected according to the used compound, for example according to the solubility of the compound. Ethanol, especially anhydrous ethanol may be a suitable solvent for most compounds. A solution of the pharmaceutical compound, in general drug, in the solvent is obtained.

An anti-solvent recrystallization process involves addition of antisolvent to create supersaturation. Without a suitable carrier, for example if the drug in the solvent is combined with water, the drug particles will aggregate resulting in poorly soluble form which is usually also poorly bioavailable. However, in the present case the process can be controlled and nanosized drug particles are obtained, which exhibit improved stability and bioavailability in the final product. When the nanostructured cellulose as described herein is provided as a carrier, a drug-nanostructured cellulose nanocomposite is formed and maintained. It was found out that the drug is not precipitated and/or aggregated in this structure but it is stabilized and released efficiently leading to good bioavailability. Such nanocomposites may be used as pharmaceutical compositions and dosage forms for different administrations. This process is described in FIG. 3 using naringenin as an exemplary drug compound and in FIG. 4 using azithromycin as an exemplary drug compounds. The process of FIG. 3 uses CNC as the carrier, and the process of FIG. 4 uses CNF as the carrier.

Figure 7:
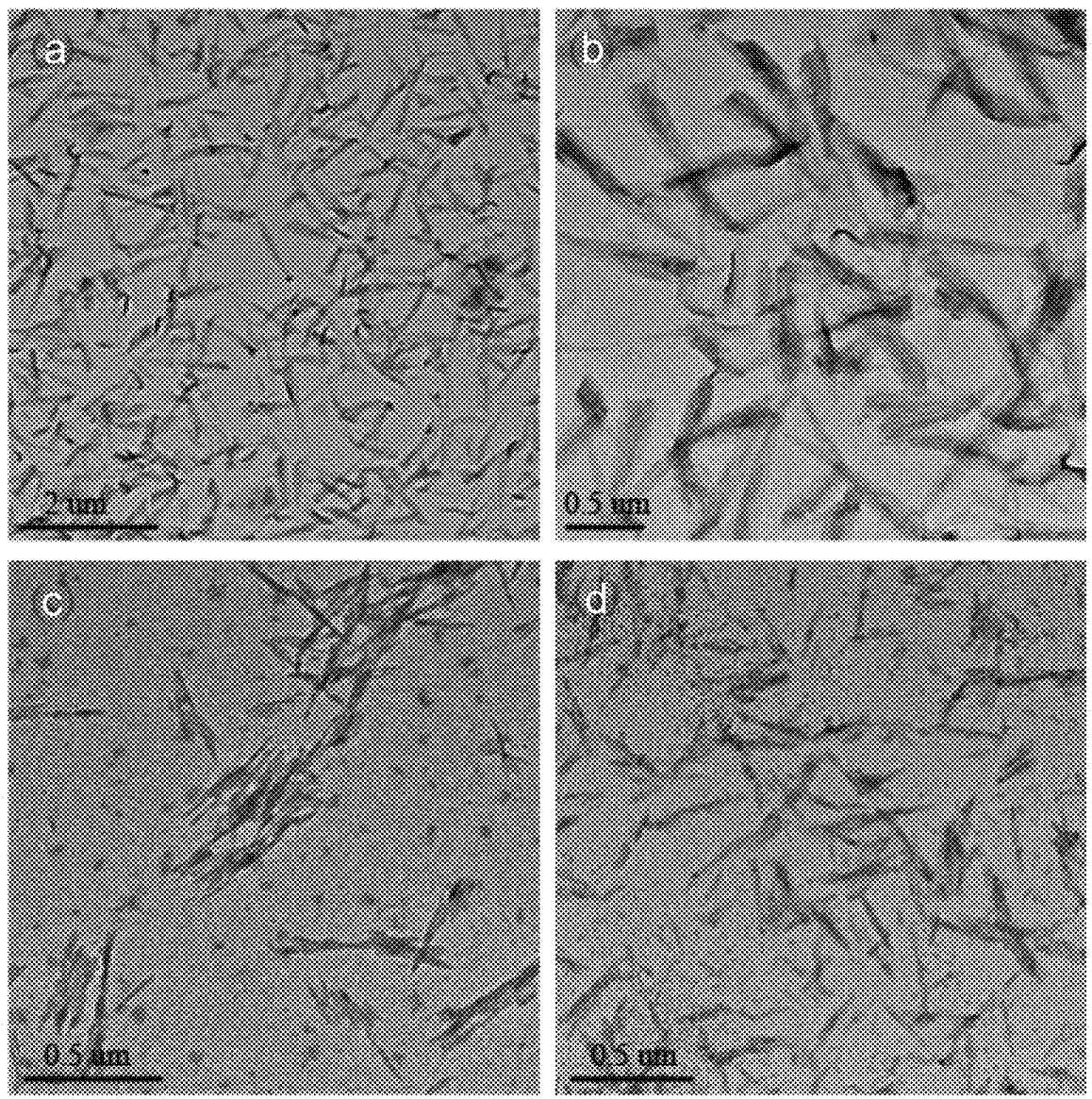
FIG. 7 shows TEM images of: (a), (b) NG particles via traditional anti-solvent recrystallization process, (c) CNC/NG nanocomposite, (d) CNC/CTAB/NG nanocomposite
Figure 12:
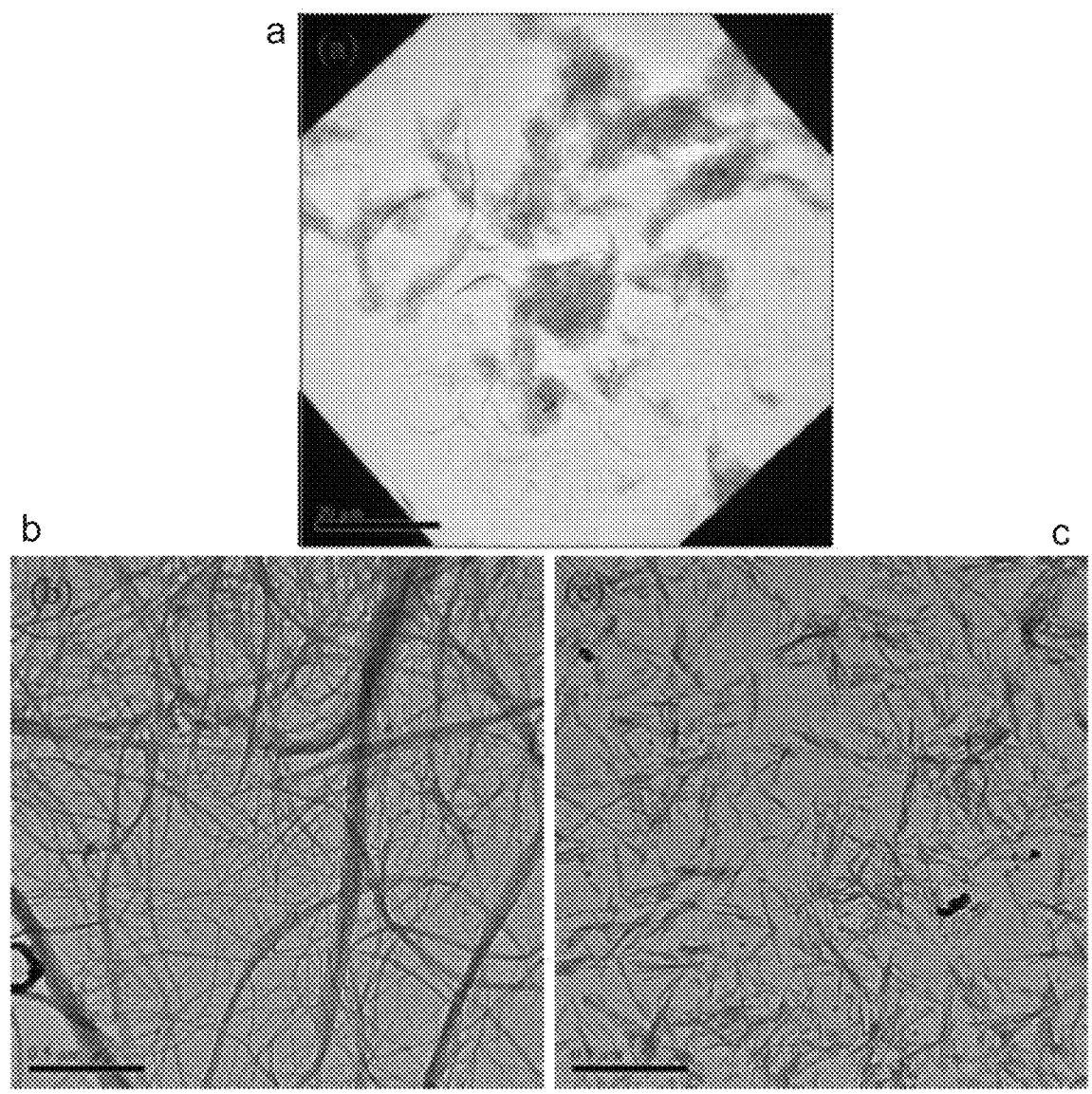
FIG. 12 shows TEM images of: (a) CNF, bar 20 μm; (b) CNF, bar 0.5 μm; (c) CNC, bar 0.5 μm
Figure 17:
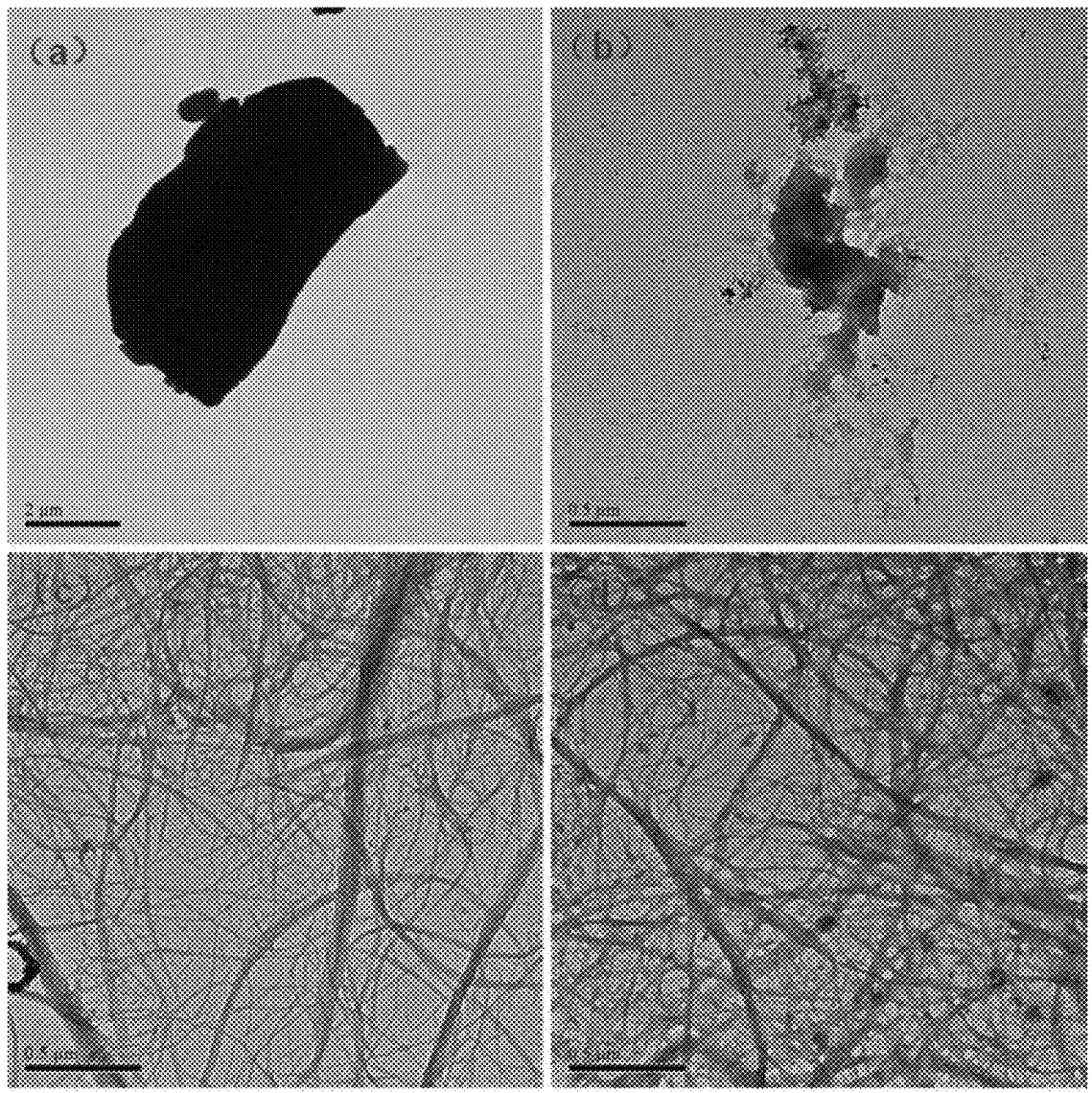
FIG. 17 shows TEM images of: (a) original AZI, (b) AZI particles (anti-solvent recrystallization process), (c) pure CNF, and (d) CNF/AZI nanocomposite.

In the method the pharmaceutical compound in the suitable solvent is added to the nanostructured cellulose in an anti-solvent process, such as described in the examples. Supersaturated concentration of the compound is obtained. The aqueous nanostructured cellulose dispersion acts as the anti-solvent. In the process the pharmaceutical compound forms nuclei at a supersaturated concentration, and then continue to grow into nanoparticles, which have an average diameter or 50 nm or less, such as 40 nm or less, 30 nm or less, or 20 nm or less. More particularly the nanoparticles are obtained in a nucleation process. The obtained nanoparticles are not present as aggregates, but rather are separate. The pharmaceutical compound is present in the nanoparticles in amorphous state rather than in highly crystalline form. The size and shape of the nanoparticles can be detected from the final product microscopically, such as by using electron microscopy, for example as shown in FIGS. 7, 12 and 17.

The pharmaceutical compound in the solvent may be combined with the aqueous dispersion of nanostructured cellulose in mixing, such as by using a mixer, agitator, disperser, homogenizer, or the like device, which may be also used for treating the nanostructured cellulose.

In one embodiment the nanostructured cellulose comprises nanofibrillar cellulose, which may have an average fibril diameter of 200 nm or less, such as in the range of 1-200 nm.

In one embodiment the nanofibrillar cellulose, when dispersed in water, provides a zero shear viscosity in the range of 1000-100000 Pa·s, such as in the range of 5000-50000 Pa·s, and a yield stress in the range of 1-50 Pa, such as in the range of 3-15 Pa, determined by rotational rheometer at a consistency of 0.5% (w/w) by weight in aqueous medium at 22° C.±1° C.

In one embodiment the nanostructured cellulose comprises nanocrystalline cellulose. Nanocrystalline cellulose may have an average fibril diameter in the range of 2-40 nm, such as 2-20 nm, and an average fibril length of 100 nm or more, up to several micrometres, such as in the range of 100-400 nm. Usually 10% or less of the material has a particle size of less than 5 μm. Nanocrystalline cellulose may be produced from cellulose by acid hydrolysis, which removes the amorphous region to obtain the crystalline region of cellulose. Therefore nanocrystalline cellulose practically consists of crystalline cellulose, and it lacks amorphous regions of cellulose. Nanofibrillar cellulose on the other hand includes both crystalline parts as straight segments and amorphous parts, which provide a kink in the fibril. Even though the both nanostructured cellulose materials have common features and properties, also because of the structural differences the two materials may also exhibit some different properties.

It was found out that the poorly soluble pharmaceutical compounds could be stabilized and the bioavailability thereof could be increased in nanostructured cellulose dispersions, even in dilute dispersions, in amounts up to 1% (w/w) or up to 1 mg per 100 μl of the pharmaceutical compound in the dispersion/composition.

The content of the pharmaceutical compound may be in the range of 0.05-1 mg per 100 μl of the pharmaceutical composition. In one example the content of the pharmaceutical compound is in the range of 0.1-0.7 mg per 100 μl of the pharmaceutical composition, such as in the range of 0.1-0.5 mg, per 100 μl of the pharmaceutical composition.

The content of the pharmaceutical compound may be in the range of 0.05-1% (w/w) of the pharmaceutical composition, such as 0.1-1% (w/w). In one example the content of the pharmaceutical compound is in the range of 0.1-0.7% (w/w), such as in the range of 0.1-0.5% (w/w).

The pharmaceutical composition may be provided as a pharmaceutical product or a pharmaceutical formulation, which may be present as a dispersion or as a hydrogel. In one example the method comprises freeze-drying the obtained pharmaceutical composition.

The method may comprise packing the obtained pharmaceutical composition into a vial, a capsule or a syringe. The pharmaceutical composition may be provided or present for example in a form or as a part of an oral dosage, a suppository, a dressing, an injectable dosage or an implant.

Oral dosage forms may be provided, for example by encapsulating or otherwise covering the aqueous dispersion of nanostructured cellulose, preferably hydrogel. This may be necessary as the nanostructured cellulose dispersion or hydrogel may not be in a form which may be provided or used as such. However, it is possible to provide the pharmaceutical composition in a gel or dispersion form, which may be applied orally by using an applicator, such as a syringe, a package, such as a tearable package, which may be formed from a membrane, sheet or otherwise flexible structure of plastic, paper or laminate thereof.

Encapsulation refers to a range of dosage forms and techniques used to enclose pharmaceuticals in a relatively stable shell known as a capsule, allowing them to, for example, be taken orally or be used as suppositories. Two main types of capsules include hard-shelled capsules and soft-shelled capsules. Hard-shelled capsules usually contain dry, powdered ingredients or miniature pellets made by e.g. processes of extrusion or spheronization. These are made in two halves: a smaller-diameter "body" that is filled and then sealed using a larger-diameter "cap". Soft-shelled capsules, primarily used for oils and for active ingredients that are dissolved or suspended in oil. The present compositions may be included in both types of capsules.

Both forms of capsules may be made from aqueous solutions of gelling agents, such as animal protein, for example gelatin, or plant polysaccharides or derivatives thereof, such as carrageenans and modified forms of starch and cellulose. Other ingredients can be added to the gelling agent solution including plasticizers such as glycerin or sorbitol to decrease the capsule's hardness, coloring agents, preservatives, disintegrants, lubricants and surface treatment.

Nanofibrillar Cellulose

The starting material for forming the hydrogel may be nanofibrillar cellulose, also called as nanocellulose, which refers to isolated cellulose fibrils or fibril bundles derived from cellulose raw material. Nanofibrillar cellulose is based on a natural polymer that is abundant in nature. Nanofibrillar cellulose has a capability of forming viscous hydrogel in water. Nanofibrillar cellulose production techniques may be based on disintegrating fibrous raw material, such as grinding of aqueous dispersion of pulp fibers to obtain nanofibrillated cellulose. After the grinding or homogenization process, the obtained nanofibrillar cellulose material is a dilute viscoelastic hydrogel.

The obtained material usually exists at a relatively low concentration homogeneously distributed in water due to the disintegration conditions. The starting material may be an aqueous gel at a concentration of 0.2-10% (w/w), for example 0.2-5% (w/w). The nanofibrillar cellulose may be obtained directly from the disintegration of fibrous raw material. An example of commercially available nanofibrillar cellulose hydrogel is GrowDex® by UPM.

Because of its nanoscale structure nanofibrillar cellulose has unique properties which enable functionalities which cannot be provided by conventional non-nanofibrillar cellulose. It is possible to prepare materials and products which exhibit different properties than conventional products or products using conventional cellulosic materials. However, because of the nanoscale structure nanofibrillar cellulose is also a challenging material. For example dewatering or handling of nanofibrillar cellulose may be difficult.

The nanofibrillar cellulose may be prepared from cellulose raw material of plant origin, or it may also be derived from certain bacterial fermentation processes. The nanofibrillar cellulose is preferably made of plant material. The raw material may be based on any plant material that contains cellulose. In one example the fibrils are obtained from non-parenchymal plant material. In such case the fibrils may be obtained from secondary cell walls. One abundant source of such cellulose fibrils is wood fibres. The nanofibrillar cellulose may be manufactured by homogenizing wood-derived fibrous raw material, which may be chemical pulp. Cellulose fibers are disintegrated to produce fibrils which have an average diameter of only some nanometers, which may be 200 nm or less in most cases, and gives a dispersion of fibrils in water. The fibrils originating from secondary cell walls are essentially crystalline with degree of crystallinity of at least 55%. Such fibrils may have different properties than fibrils originated from primary cell walls, for example the dewatering of fibrils originating from secondary cell walls may be more challenging. In general in the cellulose sources from primary cell walls, such as sugar beet, potato tuber and banana rachis, the microfibrils are easier to liberate from the fibre matrix than fibrils from wood, and the disintegration requires less energy. However, these materials are still somewhat heterogeneous and consist of large fibril bundles.

Non-wood material may be from agricultural residues, grasses or other plant substances such as straw, leaves, bark, seeds, hulls, flowers, vegetables or fruits from cotton, corn, wheat, oat, rye, barley, rice, flax, hemp, manila hemp, sisal hemp, jute, ramie, kenaf, bagasse, bamboo or reed. The cellulose raw material could be also derived from the cellulose-producing micro-organism. The micro-organisms can be of the genus *Acetobacter, Agrobacterium, Rhizobium, Pseudomonas* or *Alcaligenes*, preferably of the genus *Acetobacter* and more preferably of the species *Acetobacter xylinumor* or *Acetobacter pasteurianus*.

It was found out that nanofibrillar cellulose obtained from wood cellulose is preferable for medical or scientific products described herein. Wood cellulose is available in large amounts, and the preparation methods developed for wood cellulose enable producing nanofibrillar materials suitable for the products. The nanofibrillar cellulose obtained by fibrillating plant fibers, especially wood fibers, differs structurally from nanofibrillar cellulose obtained from microbes, and it has different properties. For example compared to bacterial cellulose, nanofibrillated wood cellulose is homogenous and more porous and loose material, which is advantageous in medical applications. Bacterial cellulose is usually used as such without similar fibrillation as in plant cellulose, so the material is different also in this respect. Bacterial cellulose is dense material which easily forms small spheroids and therefore the structure of the material is discontinuous, and it is not desired to use such material in the medical applications, especially when homogeneity of the material is required.

Wood may be from softwood tree such as spruce, pine, fir, larch, douglas-fir or hemlock, or from hardwood tree such as birch, aspen, poplar, alder, eucalyptus, oak, beech or acacia, or from a mixture of softwoods and hardwoods. In one example the nanofibrillar cellulose is obtained from wood pulp. The nanofibrillar cellulose may be obtained from hardwood pulp. In one example the hardwood is birch. The nanofibrillar cellulose may be obtained from softwood pulp. In one example said wood pulp is chemical pulp. Chemical pulp may be desired for the products disclosed herein. Chemical pulp is pure material and may be used in a wide variety of applications. For example chemical pulp lack the pitch and resin acids present in mechanical pulp, and it is more sterile or easily sterilisable. Further, chemical pulp is more flexible and provides advantageous properties for example in medical and scientific materials. For example very homogenous nanofibrillar cellulose materials may be prepared without excess processing or need for specific equipment or laborious process steps.

Nanofibrillar cellulose, including the cellulose fibrils and/or fibril bundles, is characterized by a high aspect ratio (length/diameter). The average length of nanofibrillar cellulose (the median length of particles such as fibrils or fibril bundles) may exceed 1 μm, and in most cases it is 50 μm or less. If the elementary fibrils are not completely separated from each other, the entangled fibrils may have an average total length for example in the range of 1-100 μm, 1-50 μm, or 1-20 μm. However, if the nanofibrillar material is highly fibrillated, the elementary fibrils may be completely or almost completely separated and the average fibril length is shorter, such as in the range of 1-10 μm or 1-5 μm. This applies especially for native grades of fibrils which are not shortened or digested, for example chemically, enzymatically or mechanically. However, strongly derivatized nanofibrillar cellulose may have a shorter average fibril length, such as in the range of 0.3-50 μm, such as 0.3-20 μm, for example 0.5-10 μm or 1-10 μm. Especially shortened fibrils, such as enzymatically or chemically digested fibrils, or mechanically treated material, may have an average fibril length of less than 1 μm, such as 0.1-1 μm, 0.2-0.8 μm or 0.4-0.6 μm. The fibril length and/or diameter may be estimated microscopically, for example using CRYO-TEM, SEM or AFM images.

The average diameter (width) of nanofibrillar cellulose is less than 1 μm, or 500 nm or less, such as in the range of 1-500 nm, but preferably 200 nm or less, even 100 nm or less or 50 nm or less, such as in the range of 1-200 nm, 2-200 nm, 2-100 nm, or 2-50 nm, even 2-20 for highly fibrillated material. The diameters disclosed herein may refer to fibrils and/or fibril bundles. The smallest fibrils are in the scale of elementary fibrils, the average diameter being typically in the range of 2-12 nm. The elementary nanofibrils may have about 100-200 nm long straight segments followed by sharp kinks along the fibril. These straight segments are composed of highly crystalline cellulose domains and the bending sites are formed by amorphous parts.

The dimensions and size distribution of the fibrils depend on the refining method and efficiency. In case of highly refined native nanofibrillar cellulose, the average fibril diameter, including fibril bundles, may be in the range of 2-200 nm or 5-100 nm, for example in the range of 10-50 nm. Nanofibrillar cellulose is characterized by a large specific surface area and a strong ability to form hydrogen bonds. In water dispersion, the nanofibrillar cellulose typically appears as either light or turbid gel-like material. Depending on the fiber raw material, nanofibrillar cellulose obtained from plants, especially wood, may also contain small amounts of other plant components, especially wood components, such as hemicellulose or lignin. The amount is dependent on the plant source.

In general cellulose nanomaterials may be divided into categories according to TAPPI W13021, which provides standard terms for cellulose nanomaterials. Not all of these materials are nanofibrillar cellulose. Two main categories are "Nano objects" and "Nano structured materials". Nanostructured materials include "Cellulose microcrystals" (sometimes called as CMC) having a diameter of 10-12 μm and length:diameter ratio (L/D)<2, and "Cellulose microfibrils" having a diameter of 10-100 nm and a length of 0.5-50 μm. Nano objects include "Cellulose nanofibers", which can be divided into "Cellulose nanocrystals" (CNC) having a diameter of 3-10 nm and L/D>5, and "Cellulose nanofibrils" (CNF or NFC), having a diameter of 5-30 nm and L/D>50.

Different grades of nanofibrillar cellulose may be categorized based on three main properties: (i) size distribution, length and/or diameter (ii) chemical composition, and (iii) rheological properties. These properties are not necessarily directly dependent on each other. To fully describe a grade, the properties may be used in parallel. Examples of different grades include native (chemically and/or enzymatically unmodified) NFC, oxidized NFC (high viscosity), oxidized NFC (low viscosity), carboxymethylated NFC and cationized NFC. Within these main grades, also sub-grades exist, for example: extremely well fibrillated vs. moderately fibrillated, high degree of substitution vs. low degree of substitution, low viscosity vs. high viscosity etc. The fibrillation technique and the chemical pre-modification have an influence on the fibril size distribution. Typically, non-ionic grades have wider average fibril diameter (for example in the range of 10-100 nm, or 10-50 nm) while the chemically modified grades are a lot thinner (for example in the range of 2-20 nm). Distribution is also narrower for the modified grades. Certain modifications, especially TEMPO-oxidation, yield shorter fibrils.

Depending on the raw material source, e.g. hardwood vs. softwood pulp, different polysaccharide composition exists in the final nanofibrillar cellulose product. Commonly, the non-ionic grades are prepared from bleached birch pulp, which yields high xylene content (25% by weight). Modified grades are prepared either from hardwood or softwood pulps. In those modified grades, the hemicelluloses are also modified together with the cellulose domain. Most probably, the modification is not homogeneous, i.e. some parts are more modified than others. Thus, detailed chemical analysis is usually not possible as the modified products are complicated mixtures of different polysaccharide structures.

In an aqueous environment, a dispersion of cellulose nanofibrils forms a viscoelastic hydrogel network. The gel is formed already at relatively low concentrations of for example 0.05-0.2% (w/w) by dispersed and hydrated entangled fibrils. The viscoelasticity of the NFC hydrogel may be characterized for example with dynamic oscillatory rheological measurements.

The nanofibrillar cellulose hydrogels exhibit characteristic rheological properties. For example they are shear-thinning or pseudoplastic materials, which may be considered as a special case of thixotropic behavior, which means that their viscosity depends on the speed or force by which the material is deformed. When measuring the viscosity in a rotational rheometer, the shear-thinning behavior is seen as a decrease in viscosity with increasing shear rate. The hydrogels show plastic behavior, which means that a certain shear stress (force) is required before the material starts to flow readily. This critical shear stress is often called the yield stress. The yield stress can be determined from a steady state flow curve measured with a stress controlled rheometer. When the viscosity is plotted as function of applied shear stress, a dramatic decrease in viscosity is seen after exceeding the critical shear stress. The zero shear viscosity and the yield stress are the most important rheological parameters to describe the suspending power of the materials. These two parameters separate the different grades quite clearly and thus enable classification of the grades.

The dimensions of the fibrils or fibril bundles are dependent for example on the raw material, the disintegration method and number of disintegration runs. Mechanical disintegration of the cellulose raw material may be carried out with any suitable equipment such as a refiner, grinder, disperser, homogenizer, colloider, friction grinder, pin mill, rotor-rotor disperser, ultrasound sonicator, fluidizer such as microfluidizer, macrofluidizer or fluidizer-type homogenizer. The disintegration treatment is performed at conditions wherein water is sufficiently present to prevent the formation of bonds between the fibers. A person skilled in the art can adjust the conditions for preparing nanofibrillar cellulose having desired rheological properties and fibrillation degree without undue experimenting, for example by selecting suitable disintegrating equipment, suitable starting material, suitable chemical, physical and/or enzymatic treatment, number of passes and/or energy used in the process as well as the concentration and chemical content of the obtained product.

In one example the disintegration is carried out by using a disperser having at least one rotor, blade or similar moving mechanical member, such as a rotor-rotor disperser, which has at least two rotors. In a disperser the fiber material in dispersion is repeatedly impacted by blades or ribs of rotors striking it from opposite directions when the blades rotate at the rotating speed and at the peripheral speed determined by the radius (distance to the rotation axis) in opposite directions. Because the fiber material is transferred outwards in the radial direction, it crashes onto the wide surfaces of the blades, i.e. ribs, coming one after the other at a high peripheral speed from opposite directions; in other words, it receives a plurality of successive impacts from opposite directions. Also, at the edges of the wide surfaces of the blades, i.e. ribs, which edges form a blade gap with the opposite edge of the next rotor blade, shear forces occur, which contribute to the disintegration of the fibers and detachment of fibrils. The impact frequency is determined by the rotation speed of the rotors, the number of the rotors, the number of blades in each rotor, and the flow rate of the dispersion through the device.

In a rotor-rotor disperser the fiber material is introduced through counter-rotating rotors, outwards in the radial direction with respect to the axis of rotation of the rotors in such a way that the material is repeatedly subjected to shear and impact forces by the effect of the different counter-rotating rotors, whereby it is simultaneously fibrillated. One example of a rotor-rotor disperser is an Atrex device.

Another example of a device suitable for disintegrating is a pin mill, such as a multi-peripheral pin mill. One example of such device includes a housing and in it a first rotor equipped with collision surfaces; a second rotor concentric with the first rotor and equipped with collision surfaces, the second rotor being arranged to rotate in a direction opposite to the first rotor; or a stator concentric with the first rotor and equipped with collision surfaces. The device includes a feed orifice in the housing and opening to the center of the rotors or the rotor and stator, and a discharge orifice on the housing wall and opening to the periphery of the outermost rotor or stator.

In one example the disintegrating is carried out by using a homogenizer. In a homogenizer the fiber material is subjected to homogenization by an effect of pressure. The homogenization of the fiber material dispersion to nanofibrillar cellulose is caused by forced through-flow of the dispersion, which disintegrates the material to fibrils. The fiber material dispersion is passed at a given pressure through a narrow through-flow gap where an increase in the linear velocity of the dispersion causes shearing and impact forces on the dispersion, resulting in the removal of fibrils from the fiber material. The fiber fragments are disintegrated into fibrils in the fibrillating step.

As used herein, the term "fibrillation" generally refers to disintegrating fiber material mechanically by work applied to the particles, where cellulose fibrils are detached from the fibers or fiber fragments. The work may be based on various effects, like grinding, crushing or shearing, or a combination of these, or another corresponding action that reduces the particle size. The expressions "disintegration" or "disintegration treatment" may be used interchangeably with "fibrillation".

The fiber material dispersion that is subjected to fibrillation is a mixture of fiber material and water, also herein called "pulp". The fiber material dispersion may refer generally to whole fibers, parts (fragments) separated from them, fibril bundles, or fibrils mixed with water, and typically the aqueous fiber material dispersion is a mixture of such elements, in which the ratios between the components are dependent on the degree of processing or on the treatment stage, for example number of runs or "passes" through the treatment of the same batch of fiber material.

One way to characterize the nanofibrillar cellulose is to use the viscosity of an aqueous solution containing said nanofibrillar cellulose. The viscosity may be for example Brookfield viscosity or zero shear viscosity. The specific viscosity, as described herein, distinguishes nanofibrillar cellulose from non-nanofibrillar cellulose.

In one example the apparent viscosity of the nanofibrillar cellulose is measured with a Brookfield viscometer (Brookfield viscosity) or another corresponding apparatus. Suitably a vane spindle (number 73) is used. There are several commercial Brookfield viscometers available for measuring apparent viscosity, which all are based on the same principle. Suitably RVDV spring (Brookfield RVDV-III) is used in the apparatus. A sample of the nanofibrillar cellulose is diluted to a concentration of 0.8% by weight in water and mixed for 10 min. The diluted sample mass is added to a 250 ml beaker and the temperature is adjusted to 20° C.±1° C., heated if necessary and mixed. A low rotational speed 10 rpm is used. In general Brookfield viscosity may be measured at 20° C.±1° C., at a consistency of 0.8% (w/w) and at 10 rpm.

The nanofibrillar cellulose, for example provided as a starting material in the method, may be characterized by the viscosity it provides in a water solution. The viscosity describes, for example, the fibrillation degree of the nanofibrillar cellulose. In one example the nanofibrillar cellulose when dispersed in water provides a Brookfield viscosity of at least 2000 mPa·s, such as at least 3000 mPa·s, measured at 20° C.±1° C., at a consistency of 0.8% (w/w) and at 10 rpm. In one example the nanofibrillar cellulose, when dispersed in water, provides a Brookfield viscosity of at least 10000 mPa·s measured at 20° C.±1° C., at a consistency of 0.8% (w/w) and at 10 rpm. In one example the nanofibrillar cellulose, when dispersed in water, provides a Brookfield viscosity of at least 15000 mPa·s measured at 20° C.±1° C., at a consistency of 0.8% (w/w) and at 10 rpm. Examples of Brookfield viscosity ranges of said nanofibrillar cellulose when dispersed in water include 2000-20000 mPa·s, 3000-20000 mPa·s, 10000-20000 mPa·s, 15000-20000 mPa·s, 2000-25000 mPa·s, 3000-25000 mPa·s, 10000-25000 mPa·s, 15000-25000 mPa·s, 2000-30000 mPa·s, 3000-30000 mPa·s, 10000-30000 mPa·s, and 15000-30000 mPa·s, measured at 20° C.±1° C., at a consistency of 0.8% (w/w) and at 10 rpm.

The nanofibrillar cellulose may also be characterized by the average diameter (or width), or by the average diameter together with the viscosity, such as Brookfield viscosity or zero shear viscosity. In one example nanofibrillar cellulose suitable for use in the products described herein has an average fibril diameter in the range of 1-200 nm, or 1-100 nm. In one example said nanofibrillar cellulose has an average fibril diameter in the range of 1-50 nm, such as 2-20 nm or 5-30 nm. In one example said nanofibrillar cellulose has an average fibril diameter in the range of 2-15 nm, such as in the case of TEMPO oxidized nanofibrillar cellulose.

The diameter of a fibril may be determined with several techniques, such as by microscopy. Fibril thickness and width distribution may be measured by image analysis of the images from a field emission scanning electron microscope (FE-SEM), a transmission electron microscope (TEM), such as a cryogenic transmission electron microscope (cryo-TEM), or an atomic force microscope (AFM). In general AFM and TEM suit best for nanofibrillar cellulose grades with narrow fibril diameter distribution.

A rheometer viscosity of the nanofibrillar cellulose dispersion may be measured according to one example at 22° C. with a stress controlled rotational rheometer (AR-G2, TA Instruments, UK) equipped with a narrow gap vane geometry (diameter 28 mm, length 42 mm) in a cylindrical sample cup having a diameter of 30 mm. After loading the samples to the rheometer they are allowed to rest for 5 min before the measurement is started. The steady state viscosity is measured with a gradually increasing shear stress (proportional to applied torque) and the shear rate (proportional to angular velocity) is measured. The reported viscosity (=shear stress/shear rate) at a certain shear stress is recorded after reaching a constant shear rate or after a maximum time of 2 min. The measurement is stopped when a shear rate of $1000\ s^{-1}$ is exceeded. This method may be used for determining the zero-shear viscosity.

In another example rheological measurements of the hydrogel samples were carried out with a stress controlled rotational rheometer (AR-G2, TA instruments, UK) equipped with 20 mm plate geometry. After loading the samples to the rheometer, 1 mm gap, without dilution, they were allowed to settle for 5 min before the measurement was started. The stress sweep viscosity was measured with gradually increasing shear stress in a range of 0.001-100 Pa at the frequency 10 rad/s, strain 2%, at 25° C. Storage modulus, loss modulus and yield stress/fracture strength can be determined.

It was found out that there is a minimum viscosity level require for hydrogel to retain its shape after the injection. This can be characterized by a storage modulus of 350 Pa or more, and a yield stress/fracture strength of 25 Pa or more, determined by stress controlled rotational rheometer with gradually increasing shear stress in a range of 0.001-100 Pa at a frequency 10 rad/s, strain 2%, at 25° C. A person skilled in the art can select suitable preparation method and parameters to obtain such features, even when using different types of starting materials, such as chemically modified or unmodified celluloses.

The nanofibrillar cellulose should have adequate degree of fibrillation so that the desired properties and effects are obtained. In one embodiment the nanofibrillar cellulose has an average diameter of a fibril in the range of 1-200 nm and/or, the nanofibrillar cellulose or the pharmaceutical composition, when dispersed in water, provides a storage modulus of 350 Pa or more, such as in the range of 350-5000 Pa, or preferably 350-1000 Pa, and yield stress of 25 Pa or more, such as in the range of 25-300 Pa, preferably 25-75 Pa, determined by stress controlled rotational rheometer with gradually increasing shear stress in a range of 0.001-100 Pa at a frequency 10 rad/s, strain 2%, at 25° C.

In one example the nanofibrillar cellulose, for example provided as a starting material in the method, when dispersed in water, provides a zero shear viscosity ("plateau" of constant viscosity at small shearing stresses) in the range of 1000-100000 Pa·s, such as in the range of 5000-50000 Pa·s, and a yield stress (shear stress where the shear thinning begins) in the range of 1-50 Pa, such as in the range of 3-15 Pa, determined by rotational rheometer at a consistency of 0.5% (w/w) by weight in aqueous medium at 22° C.±1° C. Such nanofibrillar cellulose may also have an average fibril diameter of 200 nm or less, such as in the range of 1-200 nm.

Turbidity is the cloudiness or haziness of a fluid caused by individual particles (total suspended or dissolved solids) that are generally invisible to the naked eye. There are several practical ways of measuring turbidity, the most direct being some measure of attenuation (that is, reduction in strength) of light as it passes through a sample column of water. The alternatively used Jackson Candle method (units: Jackson Turbidity Unit or JTU) is essentially the inverse measure of the length of a column of water needed to completely obscure a candle flame viewed through it.

Turbidity may be measured quantitatively using optical turbidity measuring instruments. There are several commercial turbidometers available for measuring turbidity quantitatively. In the present case the method based on nephelometry is used. The units of turbidity from a calibrated nephelometer are called Nephelometric Turbidity Units (NTU). The measuring apparatus (turbidometer) is calibrated and controlled with standard calibration samples, followed by measuring of the turbidity of the diluted NFC sample.

In one turbidity measurement method, a nanofibrillar cellulose sample is diluted in water, to a concentration below the gel point of said nanofibrillar cellulose, and turbidity of the diluted sample is measured. Said concentration where the turbidity of the nanofibrillar cellulose samples is measured is 0.1%. HACH P2100 Turbidometer with a 50 ml measuring vessel is used for turbidity measurements. The dry matter of the nanofibrillar cellulose sample is determined and 0.5 g of the sample, calculated as dry matter, is loaded in the measuring vessel, which is filled with tap water to 500 g and vigorously mixed by shaking for about 30 s. Without delay the aqueous mixture is divided into 5 measuring vessels, which are inserted in the turbidometer. Three measurements on each vessel are carried out. The mean value and standard deviation are calculated from the obtained results, and the final result is given as NTU units.

One way to characterize nanofibrillar cellulose is to define both the viscosity and the turbidity. Low turbidity refers to small size of the fibrils, such as small diameter, as small fibrils scatter light poorly. In general as the fibrillation degree increases, the viscosity increases and at the same time the turbidity decreases. This happens, however, until a certain point. When the fibrillation is further continued, the fibrils finally begin to break and cannot form a strong network any more. Therefore, after this point, both the turbidity and the viscosity begin to decrease.

In one example the turbidity of anionic nanofibrillar cellulose is lower than 90 NTU, for example from 3 to 90 NTU, such as from 5 to 60, for example 8-40 measured at a consistency of 0.1% (w/w) in aqueous medium, and measured by nephelometry. In one example the turbidity of native nanofibrillar may be even over 200 NTU, for example from 10 to 220 NTU, such as from 20 to 200, for example 50-200 measured at measured at 20° C.±1° C. a consistency of 0.1% (w/w) in aqueous medium, and measured by nephelometry. To characterize the nanofibrillar cellulose these ranges may be combined with the viscosity ranges of the nanofibrillar cellulose, such as zero shear viscosity, storage modulus and/or yield stress.

Nanofibrillar cellulose may be or comprise non-modified nanofibrillar cellulose. The drainage of non-modified nanofibrillar cellulose is significantly faster than for example anionic grade. Non-modified nanofibrillar cellulose generally has a Brookfield viscosity in the range of 2000-10000 mPa·s, measured at 20° C.±1° C., at a consistency of 0.8% (w/w) and at 10 rpm. It is preferred that the nanofibrillar cellulose has a suitable carboxylic acid content, such as in the range of 0.6-1.4 mmol COOH/g, for example in the range of 0.7-1.2 mmol COOH/g, or in the range of 0.7-1.0 mmol COOH/g or 0.8-1.2 mmol COOH/g, determined by conductometric titration.

The disintegrated fibrous cellulosic raw material may be modified fibrous raw material. Modified fibrous raw material means raw material where the fibers are affected by the treatment so that cellulose nanofibrils are more easily detachable from the fibers. The modification is usually performed to fibrous cellulosic raw material which exists as a suspension in a liquid, i.e. pulp.

The modification treatment to the fibers may be chemical, enzymatic or physical. In chemical modification the chemical structure of cellulose molecule is changed by chemical reaction ("derivatization" of cellulose), preferably so that the length of the cellulose molecule is not affected but functional groups are added to β-D-glucopyranose units of the polymer. The chemical modification of cellulose takes place at a certain conversion degree, which is dependent on the dosage of reactants and the reaction conditions, and as a rule it is not complete so that the cellulose will stay in solid form as fibrils and does not dissolve in water. In physical modification anionic, cationic, or non-ionic substances or any combination of these are physically adsorbed on cellulose surface.

The cellulose in the fibers may be especially ionically charged after the modification. The ionic charge of the cellulose weakens the internal bonds of the fibers and will later facilitate the disintegration to nanofibrillar cellulose. The ionic charge may be achieved by chemical or physical modification of the cellulose. The fibers may have higher anionic or cationic charge after the modification compared with the starting raw material. Most commonly used chemical modification methods for making an anionic charge are oxidation, where hydroxyl groups are oxidized to aldehydes and carboxyl groups, sulphonization and carboxymethylation. Chemical modifications introducing groups, such as carboxyl groups, which may take part in forming a covalent bond between the nanofibrillar cellulose and the bioactive molecule, may be desired. A cationic charge in turn may be created chemically by cationization by attaching a cationic group to the cellulose, such as quaternary ammonium group.

Nanofibrillar cellulose may comprise chemically modified nanofibrillar cellulose, such as anionically modified nanofibrillar cellulose or cationically modified nanofibrillar cellulose. In one example the nanofibrillar cellulose is anionically modified nanofibrillar cellulose. In one example the anionically modified nanofibrillar cellulose is oxidized nanofibrillar cellulose. In one example the anionically modified nanofibrillar cellulose is sulphonized nanofibrillar cellulose. In one example the anionically modified nanofibrillar cellulose is carboxymethylated nanofibrillar cellulose. The material obtained with the anionical modification of cellulose may be called anionic cellulose, which refers to material wherein the amount or proportion of anionic groups, such as carboxylic groups, is increased by the modification, when compared to a non-modified material. It is also possible to introduce other anionic groups to the cellulose, instead or in addition to carboxylic groups, such as phosphate groups or sulphate groups. The content of these groups may be in the same ranges as is disclosed for carboxylic acid herein.

The cellulose may be oxidized. In the oxidation of cellulose, the primary hydroxyl groups of cellulose may be oxidized catalytically by a heterocyclic nitroxyl compound, such as through N-oxyl mediated catalytic oxidation, for example 2,2,6,6-tetramethylpiperidinyl-1-oxy free radical, generally called "TEMPO". The primary hydroxyl groups (C6-hydroxyl groups) of the cellulosic β-D-glucopyranose units are selectively oxidized to carboxylic groups. Some aldehyde groups are also formed from the primary hydroxyl groups. Regarding the finding that low degree of oxidation does not allow efficient enough fibrillation and higher degree of oxidation inflicts degradation of cellulose after mechanical disruptive treatment, the cellulose may be oxidized to a level having a carboxylic acid content in the oxidized cellulose in the range of 0.5-2.0 mmol COOH/g pulp, 0.6-1.4 mmol COOH/g pulp, or 0.8-1.2 mmol COOH/g pulp, preferably to 1.0-1.2 mmol COOH/g pulp, determined by conductometric titration. When the fibers of oxidized cellulose so obtained are disintegrated in water, they give stable transparent dispersion of individualized cellulose fibrils, which may be, for example, of 3-5 nm in width. With oxidized pulp as the starting medium, it is possible to obtain nanofibrillar cellulose where Brookfield viscosity measured at a consistency of 0.8% (w/w) is at least 10000 mPa·s, for example in the range of 10000-30000 mPa·s.

Whenever the catalyst "TEMPO" is mentioned in this disclosure, it is evident that all measures and operations where "TEMPO" is involved apply equally and analogously to any derivative of TEMPO or any heterocyclic nitroxyl radical capable of catalyzing selectively the oxidation of the hydroxyl groups of C6 carbon in cellulose.

The modifications of nanofibrillar cellulose disclosed herein may also be applied to other fibrillar cellulose grades described herein. For example also highly refined cellulose or microfibrillar cellulose may be similarly chemically or enzymatically modified. However, there are differences for example in the final fibrillation degree of the materials.

In one example such chemically modified nanofibrillar cellulose, when dispersed in water, provides a Brookfield viscosity of at least 10000 mPa·s measured at 20° C.±1° C., at a consistency of 0.8% (w/w) and at 10 rpm. In one example such chemically modified nanofibrillar cellulose, when dispersed in water, provides a Brookfield viscosity of at least 15000 mPa·s measured at 20° C.±1° C., at a consistency of 0.8% (w/w) and at 10 rpm. In one example such chemically modified nanofibrillar cellulose, when dispersed in water, provides a Brookfield viscosity of at least 18000 mPa·s measured at 20° C.±1° C., at a consistency of 0.8% (w/w) and at 10 rpm. Examples of anionic nanofibrillar celluloses used have a Brookfield viscosity in the range of 13000-15000 mPa·s or 18000-20000 mPa·s, or even up to 25000 mPa·s, depending on the degree of fibrillation.

In one example the nanofibrillar cellulose is TEMPO oxidized nanofibrillar cellulose. It provides high viscosity at low concentrations, for example a Brookfield viscosity of at least 20000 mPa·s, even at least 25000 mPa·s, measured at 20° C.±1° C., at a consistency of 0.8% (w/w) and at 10 rpm. In one example the Brookfield viscosity of TEMPO oxidized nanofibrillar cellulose is in the range of 20000-30000 mPa·s, such as 25000-30000 mPa·s, measured at 20° C.±1° C., at a consistency of 0.8% (w/w) and at 10 rpm.

In one example the nanofibrillar cellulose comprises chemically unmodified nanofibrillar cellulose. In one example such chemically unmodified nanofibrillar cellulose, when dispersed in water, provides a Brookfield viscosity of at least 2000 mPa·s, or at least 3000 mPa·s, measured at 20° C.±1° C., at a consistency of 0.8% (w/w) and at 10 rpm.

Auxiliary agents for enhancing the manufacturing process or improving or adjusting the properties of the product may be included in the nanofibrillar cellulose dispersion. Such auxiliary agents may be soluble in the liquid phase of the dispersion, they may form an emulsion or they may be solid. Auxiliary agents may be added already during the manufacturing of the nanofibrillar cellulose dispersion to the raw material or they may be added to a formed nanofibrillar cellulose dispersion or gel. The auxiliary agents may be also added to the final product, for example by impregnating, spraying, dipping, soaking or the like method. The auxiliary agents are usually not covalently bound to the nanofibrillar cellulose, so they may be releasable from the nanocellulose matrix. A controlled and/or sustained release of such agents may be obtained when using NFC as matrix. Examples of auxiliary agents include therapeutic (pharmaceutic) agents and other agents affecting to the properties of the product or to the properties of the active agents, such as buffers, surfactants, plasticizers, emulsifiers or the like. In one example the dispersion contains one or more salts, which may be added to enhance the properties of the final product or to facilitate water removal from the product in the manufacturing process. Examples of salts include chloride salts, such as sodium chloride, calcium chloride and potassium chloride. The salt may be included in an amount in the range of 0.01-1.0% (w/w) of the dry matter in the dispersion. The final product may also be dipped or soaked in a solution of sodium chloride, such as in an aqueous solution of about 0.9% sodium chloride. Desired salt content in the final product may be in the range of 0.5-1%, such as about 0.9%, of the volume of the wet product. The salts, buffers and the like agents may be provided to obtain physiological conditions.

Multivalent cations may be included to obtain non-covalent crosslinking of the nanofibrillar cellulose. One example provides a nanofibrillar cellulose product comprising nanofibrillar cellulose, especially comprising anionically modified nanofibrillar cellulose, and multivalent cations, such as multivalent metal cations, for example selected from cations of calcium, barium, magnesium, zinc, aluminum, gold, platinum and titanium, wherein the nanofibrillar cellulose is crosslinked by the multivalent cations. Especially barium and calcium may be useful in biomedical application, and especially barium may be used in labelling and can be used for detecting the injected hydrogel The amount of the multivalent cations may be in the range of 0.1-3% (w/w), for example 0.1-2% (w/w) calculated from the dry content of the hydrogel.

One example provides a method for preparing such a hydrogel, the method comprising providing pulp, disintegrating the pulp until nanofibrillar cellulose is obtained, forming the nanofibrillar cellulose into a hydrogel The nanofibrillar cellulose may be fibrillated into a desired fibrillation degree and adjusted into desired water content, or otherwise modified, so that it forms a gel having desired properties as described herein. In one example the nanofibrillar cellulose in the hydrogel is anionically modified nanofibrillar cellulose.

The hydrogel to be used as a medical or scientific hydrogel needs to be homogenous. Therefore the method for preparing the hydrogel may include homogenizing a hydrogel comprising nanofibrillar cellulose, preferably with a homogenizing device such as ones described herein. With this preferably non-fibrillating homogenizing step it is possible to remove areas of discontinuity from the gel. A homogenous gel having better properties for the applications is obtained. The hydrogel may be further sterilized, for example by using heat and/or radiation, and/or by adding sterilizing agents, such as antimicrobials.

Use of the Composition

The compositions comprising pharmaceutical compound(s) in a nanostructured cellulose hydrogel disclosed herein may be used in a variety of methods comprising delivering, injecting, implanting and/or otherwise administering the composition to a subject, such as human or animal subject. The subject may be a patient, especially a patient in need of therapy which involves the pharmaceutical compound(s) included in the composition. It may be necessary to recognize or detect a subject which needs treatment. There may be a specific target in a subject whereto the pharmaceutical is targeted, for example injected. The methods include providing the composition comprising pharmaceutical compound(s) in a nanofibrillar cellulose hydrogel in a suitable form, such as in injectable form or implantable form. Also oral dosage forms may be provided, for example encapsulated in biodegradable capsules, such as soft capsules. The treatment, which may be therapy, may comprise extended-release administration of one or more pharmaceutical compound(s) such sustained-release or controlled-release administration. Analogously the pharmaceutical formulation to be administered may be extended release composition or dosage form, such as sustained-release or controlled-release composition or dosage form. The treatment may comprise any suitable therapeutic treatment, such as prolonged treatment, or treatment with one or more other suitable pharmaceutical compound(s). The pharmaceutical composition may be provided for use as a medicament for treating a subject, in general by administering to a subject by a suitable route and/or by suitable means of administration.

One example provides the pharmaceutical composition for use as a medicament for stabilizing a pharmaceutical compound having a solubility in water of 1 mg/ml or less at 25° C., for example during storage and/or when administered to a subject.

One example provides the pharmaceutical composition for use as a medicament for enhancing bioavailability of a pharmaceutical compound having a solubility in water of 1 mg/ml or less at 25° C., for example when administered to a subject.

One example provides a method for treating a subject in need of therapy, the method comprising preferably recognizing a subject in need of therapy or treatment, providing the composition comprising pharmaceutical compound(s) in a nanostructured cellulose hydrogel disclosed herein, and delivering or administering the composition to the subject.

EXAMPLES

In this study, nanocellulose (nano crystalline cellulose CNC and nanofibrillar cellulose NFC) dispersion were used as carriers for Naringenin (NG) and Azithromycin (Azi) to enhance its dissolution rate and antioxidant activity. The dissolution of Azi was significantly enhanced in contrast to the original Azi in aqueous solution, based on the formation of CNF/Azi nanocomposite. CNC/NG and CNC/CTAB/NG nanocomposites were successfully prepared based on the CNCs carriers and the anti-solvent recrystallization process.

Pure CNCs have also good hydroxyl radical (OH·) scavenging ability due to its large amount of reducing ends of cellulose. Also, it was confirmed that NFC hydrogel worked as a matrix for non-water soluble or limited water-soluble drug powders (Carprofen or Meloxicam) preventing the agglomeration and aggregation. Nanocellulose dispersions or hydrogels can improve the bioavailability of hydrophobic drugs in aqueous systems.

Figure 2:
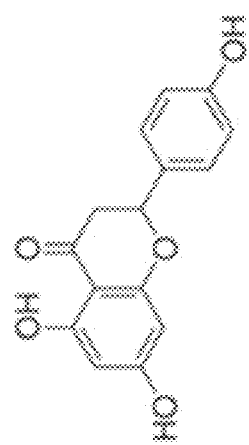
FIG. 2 shows the chemical structure of naringenin

Part I: Cellulose Nanocrystals (CNCs) as Nanocarriers for Naringenin to Enhance its Dissolution and Bioavailability 1. Background Naringenin (NG, 4,5,7-trihydroxy flavanone, FIG. 2) is a natural dihydroflavonoid compound. The NG is extracted from many kinds of natural products, such as grapefruit, tomatoes, grapes and citrus fruits. Many studies have revealed that NG has many pharmacological activities, including free radicals scavenging, anti-tumor, anti-bacterial, anti-viral, anti-inflammatory, anti-allergic, and thrombotic inhibition in vivo. However, the pharmaceutical application of NG is quite limited because of its poor water solubility and low lipid solubility.

In this study, CNCs were used as carriers for NG to enhance its dissolution rate and antioxidant activity. The NG was first nanonized through anti-solvent recrystallization and then loaded onto the CNCs to form the CNC/NG nanocomposite. Moreover, the CNCs were coated with cetyltrimethylammonium bromide (CTAB) to increase their hydrophobicity during preparation of the CNC/CTAB/NG nanocomposite. The resultant CNC/NG and CNC/CTAB/NG nanocomposites were characterized by Fourier transform infrared (FTIR) spectroscopy, transmission electron microscopy (TEM), and X-ray diffraction (XRD) analysis. The dissolution rate and in vitro antioxidant activity (OH· free radical scavenging) were also studied.

2. Research Objectives 2.1 Preparation and Characterization of CNC/NG and CNC/CTAB/NG Nanocomposites;

2.2 Evaluation of the Dissolution and Antioxidant Activity in Aqueous Systems of NG in the CNC/NG and CNC/CTAB/NG Nanocomposites.

3. Materials and Methods 3.1 Experimental Materials and Instruments

Cellulose nanocrystals (CNCs) were obtained as 98%, freeze-dried powder from Cellulose Lab Inc. (Fredericton, Canada). Naringenin (NG) was obtained as 98% purity from Aifa Biotechnology Co., Ltd(Chengdu, China)

Main experimental instruments included ultrasonic cell crusher D&DN JY99-IIDN from Xinzhi Biotechnology Co., Ltd. (Zhejiang, China), UV-vis spectrophotometer TU-1810PC from Beijing Puhua General Instrument Co., Ltd. (Beijing, China), Fourier transform infrared spectrometer Nicolet iS5 from Thermo Fisher Company (Waltham, USA), Transmission electron microscopy JEM-2010 from Electronics Corporation (Tokyo, Japan), X-Ray Diffractometer Bruker D8 Advance from Bruker Company (Karlsruhe, Germany), and Freeze-drier ALPHA1-2LDPLUS from Marin Christ company (Osterode, Germany).

3.3 Experimental Methods 3.3.1 Preparation of the CNC/NG Nanocomposite

The original NG powder was dissolved in anhydrous ethanol to form a solution with a concentration of 25 μg/ml under ultrasonic dispersion at room temperature. Subsequently, different volume of the NG ethanol solution was added dropwise into a well-dispersed CNCs aqueous solution (60 ml and 0.2 wt. %) under magnetic stirring in an ice-water bath, which was maintained for 10 min. Finally, the resultant CNC/NG nanocomposite suspension was freeze-dried for future use.

For comparison, different volume of the NG ethanol solution (25 μg/ml) was added dropwise into deionized water (60 ml) under the same conditions to prepare NG particles without CNCs (traditional anti-solvent recrystallization process).

3.3.2 Preparation of the CNC/CTAB/NG Nanocomposite

A CTAB solution with a concentration of 1 mmol/l was prepared by dissolving a certain CTAB powder in deionized water. 10 ml of the CTAB solution was added dropwise into 100 ml of CNCs aqueous solution (0.2 wt. %) under magnetic stirring at room temperature. The resultant CNC/CTAB mixture was heated to 60° C., and maintained for 30 min in the shaking table, and then cooled down to room temperature. The reaction product obtained to form a CTAB-modified CNCs precipitate, which was for subsequent use.

A certain NG ethanol solution (25 μg/ml) was added dropwise into a CTAB-modified CNCs aqueous suspension (60 ml and 0.2 wt. %) under vigorous stirring in an ice-water bath, which was maintained for 10 min. The resultant CNC/CTAB/NG nanocomposite suspension was freeze-dried for further use.

3.3.3 Fourier Transform Infrared Spectroscopy (FTIR) Analysis

Samples of CNCs, original NG powder, CNC/NG and CNC/CTAB/NG nanocomposites were analyzed and recorded on a Nicolet iS5 FTIR Spectrometer (Thermo Fisher, Waltham, USA), with scanning were collected over a range of 400 $cm^{-1}$ to 4000 $cm^{-1}$.

3.3.4 Transmission Electron Microscope (TEM) Observation

Samples of CNCs, original NG powder, CNC/NG and CNC/CTAB/NG nanocomposites were diluted with deionized water to 0.01 wt. %, and a drop of the diluted dispersion was transferred to a carbon-coated copper grid. The grid was then air-dried overnight at room temperature. TEM observations were conducted using a JEM 2010 (S) TEM instrument (Japan) operated at an accelerating voltage of 200 keV.

3.3.5 X-Ray Diffraction (XRD) Analysis

Samples of CNCs, original NG powder, CNC/NG and CNC/CTAB/NG nanocomposites were obtained on a Bruker D8 Advance powder X-ray diffractometer (Germany) operated at an acceleration voltage of 40 kV, the diffraction intensity of the Cu Kα radiation was measured over a 2θ scanning range of 3° to 50° at 0.02°/s per step.

3.3.6 In Vitro Dissolution Rate of the NG (1) Standard NG Curve

The original NG powder was dissolved in anhydrous ethanol to form a series of concentrations NG solution (2.4, 3.6, 4.8, 6.0, 7.2 and 8.4 mg/ml). Then, ultraviolet (UV) absorption measurement at a wavelength of 290 nm was conducted to determine the concentration of the NG solution, and standard NG curve can be obtained.

(2) In Vitro Dissolution Rate

The dissolution rate was determined according to the method of 2015 Chinese pharmacopoeia (XC II). Firstly, 2 mg samples of NG were placed in 100 ml of deionized water, and stirred at 100 rpm and 37° C. Then, at a prescheduled time (1, 5, 10, 20, 40, 60, 80, 100, 120 min), 5 ml of each sample was removed and filtered through a 0.22 μm membrane for UV absorption measurement at a wavelength of 290 nm to determine the NG concentration; meanwhile, 5 ml of deionized water was immediately added to the dissolution medium to keep the constant volume. The dissolution rate of NG was calculated using Eq. 1:

$$\text{Dissolution rate }(\%)=(C_n \times V_2 + C_1 \times V_1 + C_2 \times V_1 + \ldots + C_{n-1} \times V_1) \times 100\%/m \quad (1)$$

Where $C_1$, $C_2$, $C_{n-1}$, $C_n$ is the NG concentration at a prescheduled time, mg/ml; m is the total input of NG, mg; $V_1$ is the fixed sampling volume, ml; $V_2$ is the total volume of dissolution medium, ml.

3.3.7 In Vitro Antioxidant Activity

The in vitro antioxidant activity of the samples was evaluated by determining the OH· scavenging activity, according to the salicylic acid hydroxylation method. In the method, the Fenton reaction was used to generate OH·, which were then trapped by salicylic acid. The system consisted of 1.8 mM ferrisulphate (2 ml), 1.8 mM salicylic acid (1.5 ml), and 1 ml of samples solution. Finally, 0.1 ml of $H_2O_2$ (0.03 wt. %) was added to the mixture solution and started the reaction, the mixture was incubated at 37° C. for 30 min. After the incubation, the UV absorption was measured at a wavelength of 510 nm. The OH· scavenging rate was calculated using Eq. 2:

$$\text{OH· scavenging rate }(\%)=(A_0-A_i)\times 100\%/A_0 \quad (2)$$

Where $A_0$ is the UV absorbance of the control, representing the total amount of OH· generated, and $A_i$ is the UV absorbance of the samples.

Figure 3:
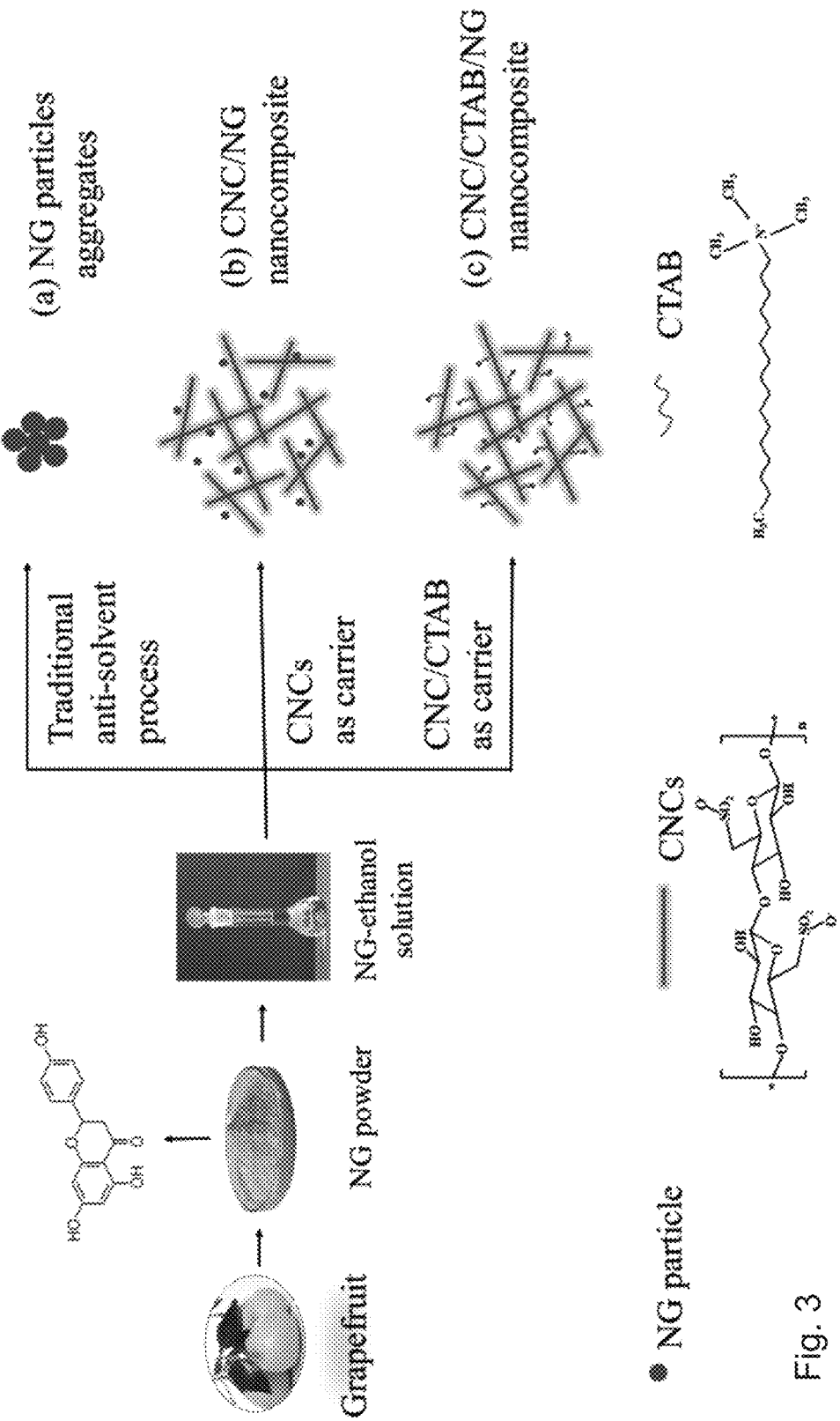
FIG. 3 shows a concept of preparing the CNC/NG and CNC/CTAB/NG nanocomposites

4. Results and Discussion 4.1 Concept of Preparing the CNC/NG and CNC/CTAB/NG Nanocomposites The flow chart for preparing the CNC/NG and CNC/CTAB/NG nanocomposites is shown in FIG. 3. In the traditional anti-solvent recrystallization process (FIG. 3, a), a NG ethanol solution was added dropwise into deionized water under different conditions. With the increase of NG dosage in the anti-solvent, the NG nuclei formed at a supersaturated concentration, and then continued to grow into NG nanoparticles. Because of its hydrophobic nature, the NG nanoparticles flocculated and formed NG aggregates, which were difficult to disperse in aqueous solutions.

As carriers, CNCs provided more sites for the NG nuclei because of their large surface area and abundant hydrogen bonds, which resulted in the formation of smaller and even NG nanoparticles (FIG. 3, b). Moreover, the excellent hydrophilicity of the CNCs allowed the CNC/NG system to be quite stable, which lowered the flocculation and aggregation of the resultant NG nanoparticles. The use of polymers and surfactants as stabilizers can inhibit/lower the particle growth of hydrophobic griseofulvin, such as poly (vinylpyrrolidone), hydroxypropyl methyl cellulose, Tween 80, and sodium dodecyl sulfate.

After CTAB modification, the CNCs became more hydrophobic and had a better compatibility with the NG molecules because of the presence of long carbon chains of CTAB. It was easier to load NG nanoparticles on the CNCs via electrostatic and hydrophobic interactions (FIG. 3, c), which can further lower the particle size and improve the stability of the NG nanoparticles.

4.2 Optimization of CNC/NG Nanocomposite Preparation 4.2.1 Factors and Levels for Orthogonal Experiment Based on their previous experiments, the inventors found that for CNC/NG nanocomposite, four factors have important influences on the hydroxyl radical (OH·) scavenging rate, including pH value, volume ratio of solvent and anti-solvent, temperature, and concentration of NG. In the following work, these four factors and their different levels will be determined for orthogonal experiment, shown in Table 2.

TABLE 2

Factors and levels for orthogonal experiment

| Levels | pH (A) | Solvent/ anti-solvent | Temperature/ ° C. | Concentration/ μg/ml |
|---|---|---|---|---|
| 1 | 5.5 | 1:10 | 20 | 20 |
| 2 | 7 | 1:30 | 60 | 5 |
| 3 | 8.5 | 1:20 | 0 | 10 |
| 4 | 10 | 1:5 | 40 | 40 |

4.2.2 Results and Analysis of the Orthogonal Experiment

L16 (4^5) table was used for the orthogonal experiment, and the OH· scavenging rate was used as evaluation indicator of the CNC/NG nanocomposite. The results and analysis of orthogonal experiment were shown in Table 3.

TABLE 3

Results and analysis of the orthogonal experiment

| Numbers | A | B | C | D | Blank | Schemes | OH• scavenging rate, % |
|---|---|---|---|---|---|---|---|
| 1 | 1 | 1 | 1 | 1 | 1 | $A_1B_1C_1D_1$ | 27.4 |
| 2 | 1 | 2 | 2 | 2 | 2 | $A_1B_2C_2D_2$ | 21.22 |
| 3 | 1 | 3 | 3 | 3 | 3 | $A_1B_3C_3D_3$ | 39.13 |
| 4 | 1 | 4 | 4 | 4 | 4 | $A_1B_4C_4D_4$ | 26.81 |
| 5 | 2 | 1 | 2 | 3 | 4 | $A_2B_1C_2D_3$ | 37.74 |
| 6 | 2 | 2 | 1 | 4 | 3 | $A_2B_2C_1D_4$ | 30.23 |
| 7 | 2 | 3 | 4 | 1 | 2 | $A_2B_3C_4D_1$ | 38.57 |
| 8 | 2 | 4 | 3 | 2 | 1 | $A_2B_4C_3D_2$ | 30.82 |
| 9 | 3 | 1 | 3 | 4 | 2 | $A_3B_1C_3D_4$ | 37.3 |
| 10 | 3 | 2 | 4 | 3 | 1 | $A_3B_2C_4D_3$ | 30.35 |
| 11 | 3 | 3 | 1 | 2 | 4 | $A_3B_3C_1D_2$ | 38.56 |
| 12 | 3 | 4 | 2 | 1 | 3 | $A_3B_4C_2D_1$ | 35.55 |
| 13 | 4 | 1 | 4 | 2 | 3 | $A_4B_1C_4D_2$ | 36.69 |

TABLE 3-continued

Results and analysis of the orthogonal experiment

| Numbers | A | B | C | D | Blank | Schemes | OH• scavenging rate, % |
|---|---|---|---|---|---|---|---|
| 14 | 4 | 2 | 3 | 1 | 4 | $A_4B_2C_3D_1$ | 36.94 |
| 15 | 4 | 3 | 2 | 4 | 1 | $A_4B_3C_2D_4$ | 44 |
| 16 | 4 | 4 | 1 | 3 | 2 | $A_4B_4C_1D_3$ | 37.78 |
| $K_1$ | 114.56 | 139.13 | 133.97 | 138.46 | 132.57 | | |
| $K_2$ | 137.36 | 118.74 | 138.51 | 127.29 | 134.87 | | |
| $K_3$ | 141.76 | 160.26 | 144.19 | 145 | 141.6 | | |
| $K_4$ | 155.41 | 130.96 | 132.42 | 138.34 | 140.05 | | |
| $k_1$ | 28.64 | 34.7825 | 33.4925 | 34.615 | 33.1425 | | |
| $k_2$ | 34.34 | 29.685 | 34.6275 | 31.8225 | 33.7175 | | |
| $k_3$ | 35.44 | 40.065 | 36.0475 | 36.25 | 35.4 | | |
| $k_4$ | 38.8525 | 32.74 | 33.105 | 34.585 | 35.0125 | | |
| Ranges (R) | 10.2125 | 10.38 | 2.9425 | 4.4275 | 2.2575 | | |
| Order | B > A > D > C | | | | | | |
| Optimal scheme | $B_3A_4D_3C_3$ | | | | | | |

Based on the results and analysis of the orthogonal experiment, the combination of $B_3A_4D_3C_3$ is the optimal choice, and the detailed conditions for preparing the CNC/NG are as follows: solvent/anti-solvent volume ratio, 1:20; pH, 10; temperature, 0° C.; concentration of NG, 10 μg/ml.

However, considering the pH value of 10 is higher than the normal pH of human body, the pH of 7.0-8.5 will be used for the following preparation of CNC/NG nanocomposite, according to the trend of pH influence on OH· scavenging rate.

4.3 Characterization 4.3.1 FTIR Analysis

Figure 5:
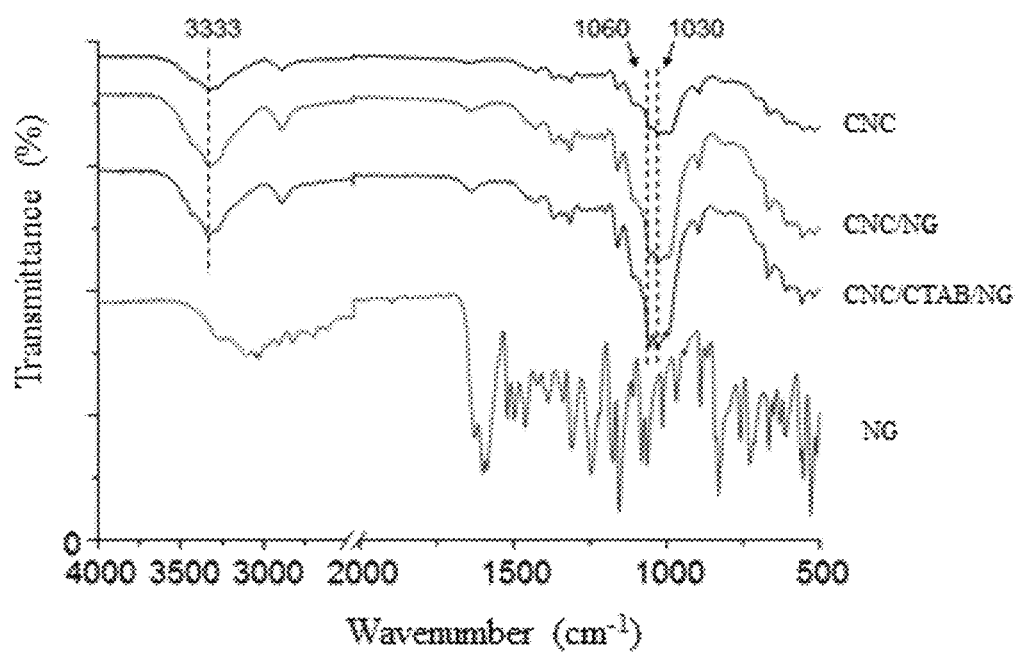
FIG. 5 shows FTIR spectrum of the CNCs, original NG, CNC/NG, and CNC/CTAB/NG nanocomposites

The FTIR spectrum of the CNCs, original NG, CNC/NG, and CNC/CTAB/NG nanocomposites are shown in FIG. 5. The absorption peaks at 3267 cm$^{-1}$, and 1600 cm$^{-1}$ are typical peaks of the original NG, representing the C—H stretching, and C=O stretching, respectively. The CNCs show the typical peaks at 3333 cm$^{-1}$ (O—H stretching), 1060 cm$^{-1}$ (secondary hydroxyl), 1030 cm$^{-1}$ (primary hydroxyl), which is accord with the characteristic of cellulose.

In contrast, for the CNC/NG nanocomposite, the absorption peaks at 3333 cm-1, 1060 cm-1, and 1030 cm-1 increased, indicative of the formation of hydrogen bonds between the CNCs and NG. Moreover, typical absorption peaks of the NG were found in the CNC/NG nanocomposite.

For the CNC/CTAB/NG nanocomposite, the absorption peaks at 1030 cm-1, and 1060 cm-1 were further increased compare with the CNC/NG nanocomposite, which can be attributed to the attachment of long alkyl chains from the CTAB onto the CNCs. Also, the typical absorption peaks of the NG were found in the CNC/CTAB/NG nanocomposite, indicating that NG was successfully loaded on the CNCs.

Figure 6:
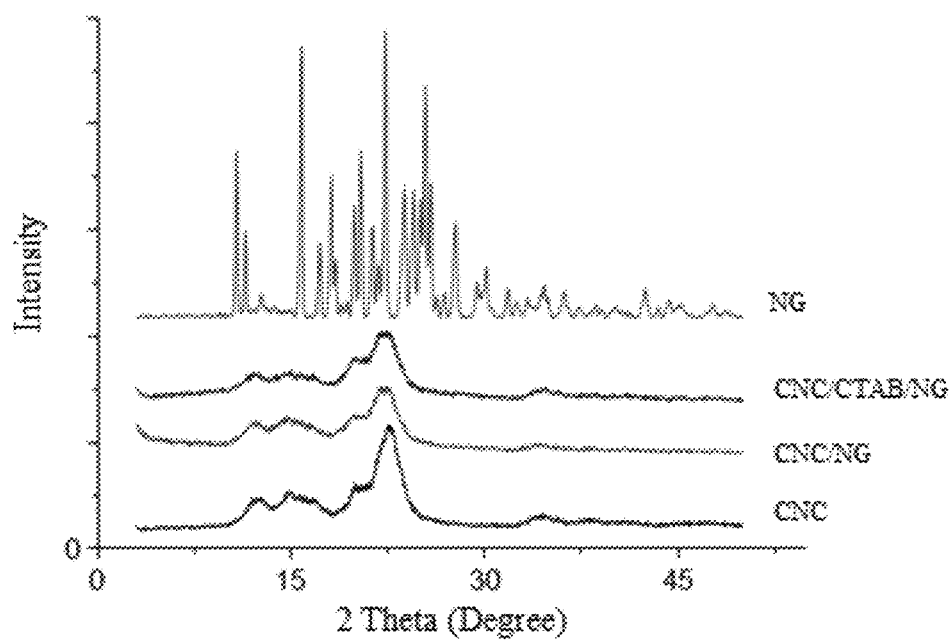
FIG. 6 shows XRD patterns of CNCs, original NG, CNC/NG, and CNC/CTAB/NG nanocomposites

FIG. 5 shows FTIR spectrum of the CNCs, original NG, CNC/NG, and CNC/CTAB/NG nanocomposites FIG. 6 shows XRD patterns of CNCs, original NG, CNC/NG, and CNC/CTAB/NG nanocomposites The XRD patterns of the CNCs, original NG, CNC/NG, and CNC/CTAB/NG nanocomposites are shown in FIG. 6. As shown, the original NG showed intense diffraction peaks at 2θ=10.76°, 15.92°, 17.24°, 18.15°, 19.90°, 20.52°, 22.20°, 23.80°, 24.43°, 25.34°, and 27.71°, indicating that NG was in a crystalline state.

In contrast, for the CNC/NG and CNC/CTAB/NG nanocomposites, the intense diffraction peaks of the NG disappeared, indicating that the NG transformed from a highly crystalline state to an amorphous state. The effective nanonization of the NG based on the formation of CNC/NG and CNC/CTAB/NG nanocomposites could be responsible for the transformation of the crystalline state of the NG.

4.3.3 TEM Analysis

It can be seen that the NG particles, prepared by traditional anti-solvent recrystallization method, were needlelike, with a length of 0.8-1.0 μm (FIGS. 7a and b).

FIG. 7 shows TEM images of: (a), (b) NG particles via traditional anti-solvent recrystallization process, (c) CNC/NG nanocomposite, (d) CNC/CTAB/NG nanocomposite In contrast, the NG particles were transformed into a number of small nanoparticles based on the formation of the CNC/NG nanocomposite (FIG. 7c). It is assumed that the CNCs provided more sites for the NG nuclei because of their large surface area and abundant hydrogen bonds, which resulted in the formation of smaller and even NG nanoparticles.

Moreover, the NG particles were further dispersed and nanonized based on the formation of the CNC/CTAB/NG nanocomposite (FIG. 7d), which can be attributed to the increased hydrophobicity of the CNCs after the CTAB modification. The nanonization of a hydrophobic drug can help to enhance its dissolution rate and bioavailability because of the increased specific surface area.

4.4 In Vitro Dissolution Rate 4.4.1 the Standard NG Curve

Different concentrations of NG ethanol solution (2.4~8.4 μg/ml) were prepared, and the UV absorption at 290 nm was measured. The standard curve of NG was plotted.

It was shown that the equation of between NG absorbance and concentration is Y=0.00761X−0.0225, and $R^2$=0.9955. The concentration and absorbance of NG showed a good linear relation, which can be used for the determination of NG concentration.

4.4.2 In Vitro Dissolution Rate

Figure 8:
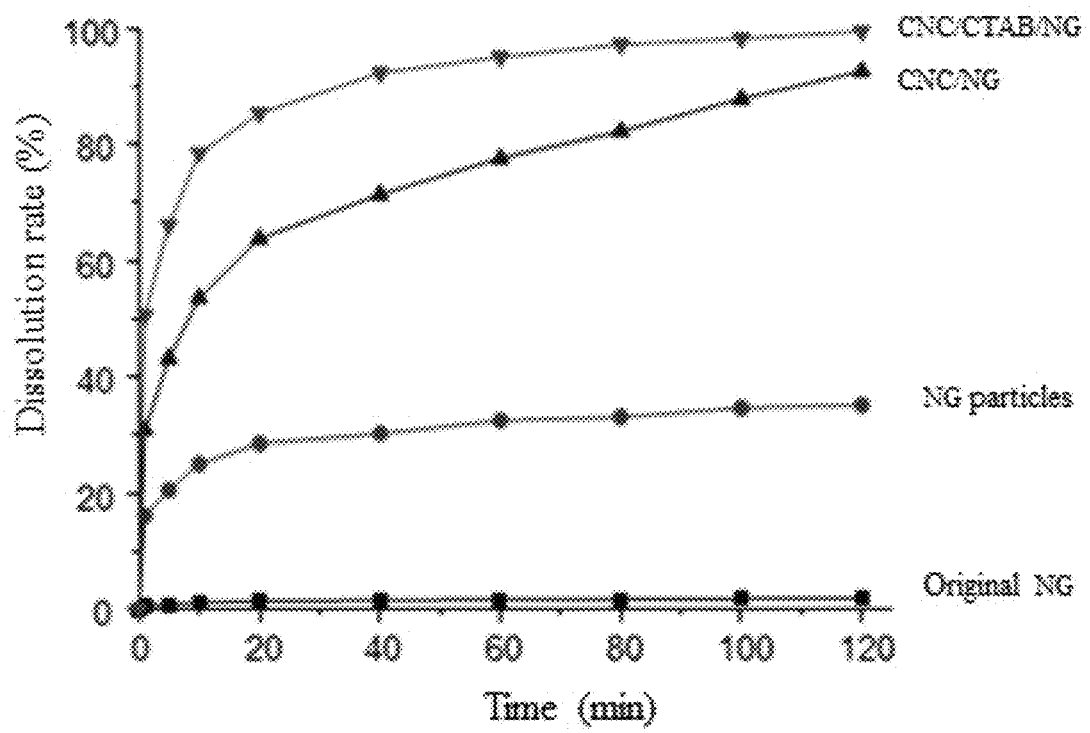
FIG. 8 shows dissolution rates of original NG, NG particles (traditional anti-solvent recrystallization process), CNC/NG and CNC/CTAB/NG nanocomposites

The dissolution rates of the original NG, NG particles (traditional anti-solvent recrystallization process), CNC/NG, and CNC/CTAB/NG nanocomposites are shown in FIG. 8. The original NG had a very limited dissolution rate, only 1.87% at 120 min. The dissolution rate of NG particles (traditional anti-solvent recrystallization process) increased, and reached 25.1% and 35.2% at 10 min and 120 min, respectively.

In contrast, for the CNC/NG and CNC/CTAB/NG nanocomposites, the dissolution rates of the NG obviously increased. For example, the dissolution rate of the CNC/NG and CNC/CTAB/NG nanocomposites reached 53.6%, and 78.5% at 10 min, respectively; subsequently, the dissolution rate increased slowly and reached 92.6%, and 99.5% at 120 min, respectively. The dissolution rate is well related to the bioavailability of hydrophobic drugs. In the literature, many researchers have reported that the bioavailability of hydrophobic drugs, such as quercetin and curcumin, can be effectively enhanced by increasing their dissolution rate.

Figure 9:
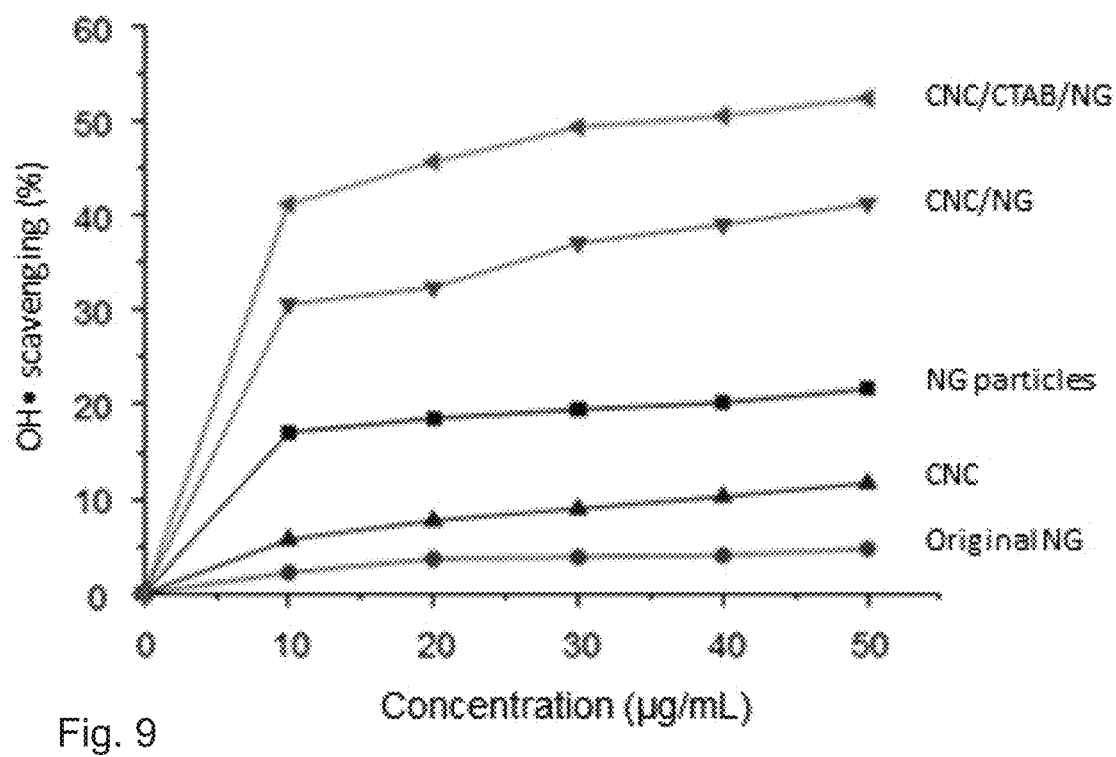
FIG. 9 shows OH· scavenging activities of original NG, NG particles (traditional anti-solvent recrystallization process), CNCs, CNC/NG and CNC/CTAB/NG nanocomposite.

FIG. 8 shows dissolution rates of original NG, NG particles (traditional anti-solvent recrystallization process), CNC/NG and CNC/CTAB/NG nanocomposites 4.5 In Vitro Hydroxyl Radical (OH·) Scavenging Activity The OH· scavenging activities of the original NG, NG particles (traditional anti-solvent recrystallization process), CNCs, CNC/NG and CNC/CTAB/NG nanocomposites are shown in FIG. 9.

It can be observed that pure CNCs showed good OH· scavenging efficiency. For example, the OH· scavenging rate is from 17.1% to 21.6% under the concentration of 10 to 50 μg/ml, which can be attributed to the large amount of reducing end groups of the CNCs.

The OH· scavenging rate of the original NG was quite low, only 6.7% at a concentration of 50 μg/ml, which is due to the hydrophobic nature of original NG. For the NG particles (anti-solvent recrystallization process), the OH· scavenging rate increased and reached 11.2% at a concentration of 50 μg/ml.

FIG. 9 shows OH· scavenging activities of original NG, NG particles (traditional anti-solvent recrystallization process), CNCs, CNC/NG and CNC/CTAB/NG nanocomposite.

In contrast, for the CNC/NG and CNC/CTAB/NG nanocomposites, the OH· scavenging rate obviously increased to 41.2% and 52.5% at a concentration of 50 μg/ml, respectively. These results indicated that the CNC and CNC/CTAB as a carrier can effectively enhance the dissolution of NG. Furthermore, the CNC/CTAB/NG nanocomposite showed better OH· scavenging rate than that of CNC/NG nanocomposite, which can be attributed to the enhanced compatibility of CTAB modified CNCs.

5. Conclusions 5.1 CNC/NG and CNC/CTAB/NG nanocomposites were successfully prepared based on the CNCs carriers and the anti-solvent recrystallization process. TEM and XRD analysis showed that the NG was effectively nanonized, well dispersed, and transformed from a highly crystalline state to an amorphous state.

5.2 Pure CNCs have good hydroxyl radical (OH·) scavenging ability due to its large amount of reducing ends of cellulose.

5.3 The dissolution rate of the NG in the CNC/NG and CNC/CTAB/NG nanocomposites obviously increased to 92.6% and 99.5% at 120 min, respectively, compared with that of the original NG (1.87%). As a result, the OH· scavenging rates of CNC/NG and CNC/CTAB/NG nanocomposites were obviously enhanced, compared with that of the original NG.

Based on these experimental results, the CNCs as carriers are promising for enhancing the bioavailability of NG because of the facile preparation method and good biocompatibility.

Part II: CNF as Nanocarrier for Azithromycin to Enhance its Dissolution and Bioavailability 1. Background Azithromycin (AZI, FIG. 10) is a 15-membered ring semi-synthetic macrolide antibiotic, which is characterized by the insertion of a nitrogen atom into a 14-membered ring to form a 15-membered ring. AZI has strong anti-bacterial activities of macrolides against gram-positive bacteria and gram-negative bacteria. Clinically, AZI has been widely used for treating respiratory tract infection, skin and soft tissue infection, and urinary and reproductive system infection. However, like other water-insoluble drugs, the main challenges of AZI in pharmacy are its insolubility in water solution and poor oral bioavailability because of its hydrophobic nature. Therefore, the most important thing for AZI is to enhance its drug release and bioavailability in aqueous system.

Figure 10:
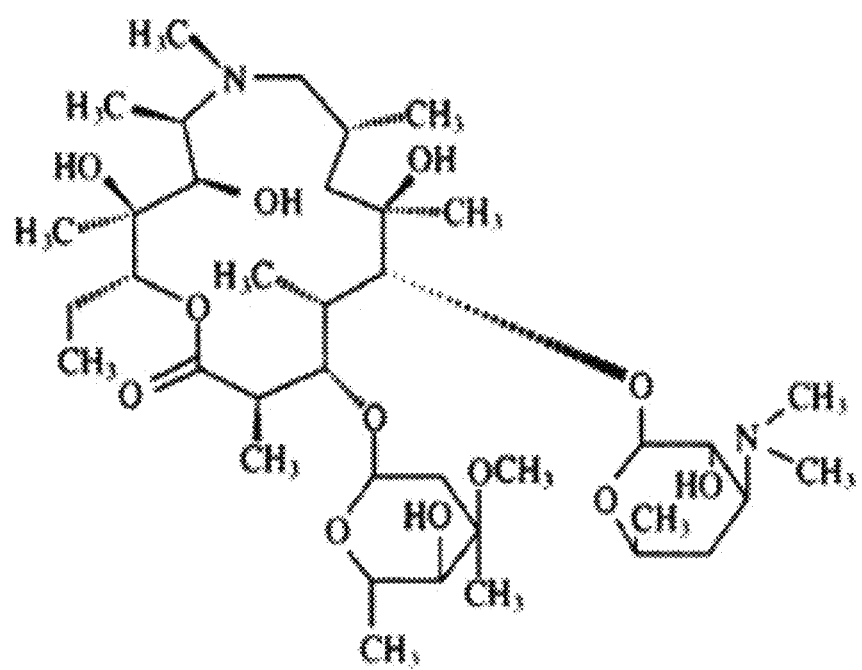
FIG. 10 shows the chemical structure of azithromycin

In this study, AZI was chosen as a model drug, and the cellulose nanofiber (CNF) provided by UPM was used as a drug carrier. The CNF/AZI nanocomposite was prepared via the anti-solvent recrystallization process to enhance the dissolution and bioavailability of AZI. FIG. 10 shows the chemical structure of azithromycin.

2. Research Objectives 2.1 Preparation and Characterization of CNF/AZI Nanocomposite;

2.2 Evaluation of the Dissolution in Aqueous System of AZI in the CNF/AZI Nanocomposite 3. Materials and Methods 3.1 Materials and Instruments Cellulose nanofiber (CNF) was obtained as 1.5% gel from UPM. Cellulose nanocrystals (CNCs) were obtained as 98%, Freeze-dried powder from Cellulose Lab Inc. (Fredericton, Canada). Azithromycin was obtained as 98% Purity from Yuanzhi Biotechnology Co., Ltd. (Nanjing, China).

Main experimental instruments included ultrasonic cell crusher D&DN JY99-IIDN from Xinzhi Biotechnology Co., Ltd. (Zhejiang, China), UV-vis spectrophotometer TU-1810PC from Beijing Puhua General Instrument Co., Ltd. (Beijing, China), Fourier transform infrared spectrometer Nicolet iS5 from Thermo Fisher Company (Waltham, USA), Transmission electron microscopy JEM-2010 from Electronics Corporation (Tokyo, Japan), X-Ray Diffractometer Bruker D8 Advance from Bruker Company (Karlsruhe, Germany), and Freeze-drier ALPHA1-2LDPLUS from Marin Christ company (Osterode, Germany).

3.2 Experimental Methods 3.2.1 Preparation of CNF/AZI Nanocomposite

The original AZI powder was dissolved in anhydrous ethanol to form a solution with a concentration of 200 μg/ml under ultrasonic dispersion at room temperature. Subsequently, 3 ml of the AZI ethanol solution was added dropwise into a well-dispersed CNF aqueous solution (60 ml, 0.05 wt. %) under magnetic stirring in an ice-water bath, which was maintained for 10 min. Finally, the resultant CNF/AZI nanocomposite suspension was freeze-dried for future use.

For comparison, 3 ml of the AZI ethanol solution (200 μg/ml) was added dropwise into deionized water (60 ml) under the same conditions to prepare AZI particles (traditional anti-solvent recrystallization process).

3.2.2 Characterization (1) Fourier Transform Infrared Spectroscopy (FTIR) Analysis Samples of CNF, original AZI powder, CNF/AZI nanocomposite were analyzed on a Nicolet iS5 FTIR Spectrometer (Thermo Fisher, Waltham, USA), with scanning were collected in a range of 400 $cm^{-1}$ to 4000 $cm^{-1}$.

(2) Transmission Electron Microscope (TEM) Observation

Samples of CNF, original AZI powder, CNF/AZI nanocomposite were diluted with deionized water to 0.01 wt. %, and a drop of the diluted dispersion was transferred to a carbon-coated copper grid. The grid was then air-dried overnight at room temperature. TEM observations were conducted using a JEM 2010 (S) TEM instrument (Japan), operated at an accelerating voltage of 200 keV.

(3) X-Ray Diffraction (XRD) Analysis

Samples of CNF, original AZI powder, CNF/AZI nanocomposite were analyzed on a Bruker D8 Advance powder X-ray diffractometer (Germany) operated at an acceleration voltage of 40 kV. The diffraction intensity of the Cu Kα radiation was measured in a 2θ scanning range of 3° to 50° at 0.02°/s per step.

3.2.3 In Vitro Hydroxyl Radical (OH·) Scavenging Activity

The in vitro antioxidant activity of the samples was evaluated by determining the OH· scavenging activity, according to the salicylic acid hydroxylation method. In the method, the Fenton reaction was used to generate OH·, which were then trapped by salicylic acid. The system consisted of 1.8 mM ferrisulphate (2 ml), 1.8 mM salicylic acid (1.5 ml), and 1 ml of samples solution. Finally, 0.1 ml of $H_2O_2$ (0.03 wt. %) was added to the mixture solution and started the reaction, the mixture was incubated at 37° C. for 30 min. After the incubation, the UV absorption was measured at a wavelength of 510 nm.

The OH· scavenging rate was calculated using Eq. 1:

$$\text{OH· scavenging rate (\%)} = (A_0 - A_i) \times 100\% \, A_0 \quad (1)$$

Where $A_0$ is the UV absorbance of the control, representing the total amount of OH· generated, and $A_i$ is the UV absorbance of the samples.

3.2.4 In Vitro Dissolution of the AZI (1) Standard AZI Curve

The original AZI powder was dissolved in anhydrous ethanol to form a solution with a concentration of 2 mg/ml under ultrasonic dispersion at room temperature. Subsequently, hydrochloric acid (0.1 M) was added into the AZI solution to form a series of AZI solution with different concentrations (16, 32, 48, 64, 80, 96 µg/ml). Then, 5 ml of each AZI sample and 5 ml of sulfuric acid (73.5%) were added into a test tube and mixed, after that the resultant mixture was kept for reaction for 30 min at the room temperature. Finally, UV absorption was measured at a wavelength of 482 nm to determine the concentration of the AZI solution, and a standard AZI curve can be plotted.

(2) In Vitro Dissolution Rate

The dissolution rate was determined according to the method of 2015 Chinese pharmacopoeia (XC II). Firstly, 2 mg of AZI was placed in 100 ml of deionized water, and stirred at 100 rpm and 37° C. At a prescheduled time (1, 5, 10, 30, 60, 120 min), 3 ml of each sample was removed and filtered through a 0.45 µm membrane to get a filtrate; meanwhile, 3 ml of deionized water was immediately added to the dissolution medium to keep the constant volume.

Then, 2 ml sulfuric acid (73.5%) and 2 ml of the resultant filtrate were added to a test tube to form a mixture, and the mixture was kept for 30 min. Finally, UV absorption was measured at a wavelength of 482 nm to determine the AZI concentration. The dissolution rate of AZI was calculated using Eq. 2:

$$\text{Dissolution rate (\%)} = (C_n \times V_2 + C_1 \times V_1 + C_2 \times V_1 + \ldots + C_{n-1} \times V_1) \times 100\%/m \quad (2)$$

Where $C_1$, $C_2$, $C_{n-1}$, $C_n$ is the AZI concentration at a prescheduled time, mg/ml; m is the total input of AZI, mg; $V_1$ is the fixed sampling volume, ml; $V_2$ is the total volume of dissolution medium, ml.

4. Results and Discussion 4.1 Characterization of CNF

In this study, the CNF from UPM R&D Center was analyzed and compared with the CNCs, including dispersion and stability in aqueous system, FTIR analysis, TEM observation, and XRD analysis. The results are as follows.

4.1.1 CNF Dispersion and Stability in Aqueous System

Figure 11:
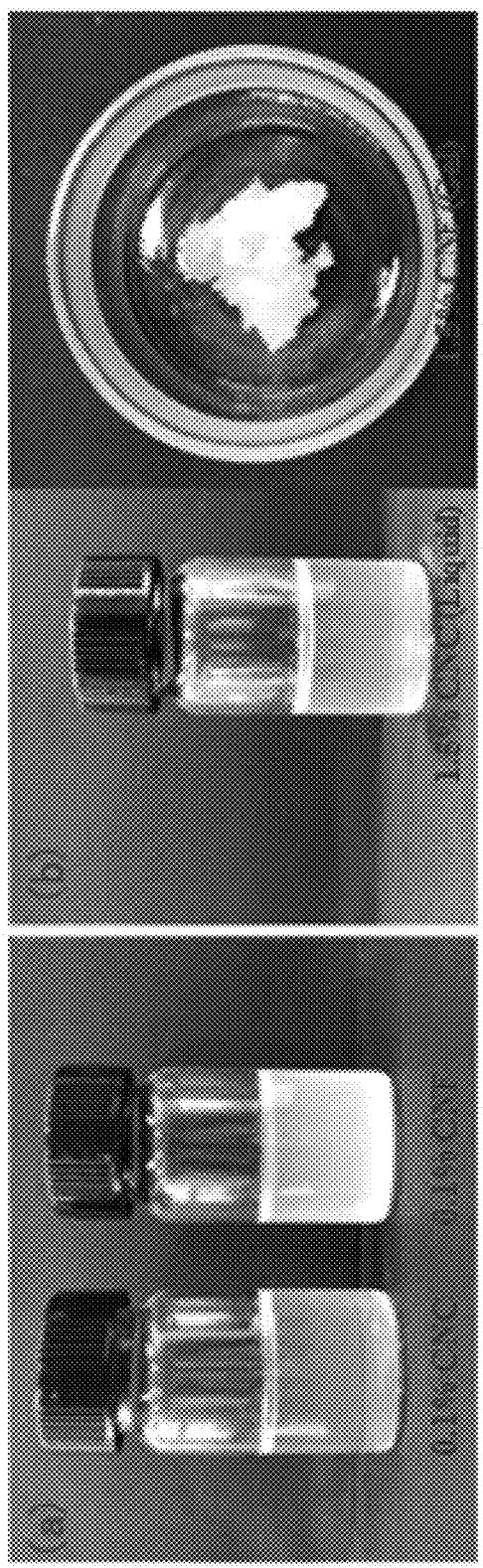
FIG. 11 shows dispersion and stability of the CNF and CNC in aqueous systems: (a) 0.1% CNC on the left and 0.1% CNF on the right, (b) 1.5% CNC (liquid) on the left, 1.5% CNF (gel) on the right.

As shown in FIG. 11*a*, the CNF is easy to be dispersed in deionized water at the concentration of 0.1 wt. %, however the dispersity and stability of the CNF suspension are lower than those of the CNCs suspension (Cellulose Lab Inc. Fredericton, Canada, produced by a sulfuric acid hydrolysis method). In FIG. 11*b*, the CNF becomes a gel and loses fluidity at a concentration of 1.5 wt. %; for comparison, the CNCs still shows good fluidity and stability at a concentration of 1.5 wt. %.

4.1.2 TEM Analysis of CNF

FIGS. 12*a* and *b* show that the CNF is characteristic of typical cellulose nanofiber, with large length and small diameter (5-50 nm). The CNF is easy to form agglomeration due to the large length and good flexibility. In contrast, the CNC is needle-like, with a length of 100-400 nm and a width of 5-40 nm (FIG. 12*c*). Compared with the CNF, CNC has a shorter length and strong rigidity, which is easy to be dispersed to form a stable suspension.

4.1.3 FTIR Analysis of the CNF

Figure 13:
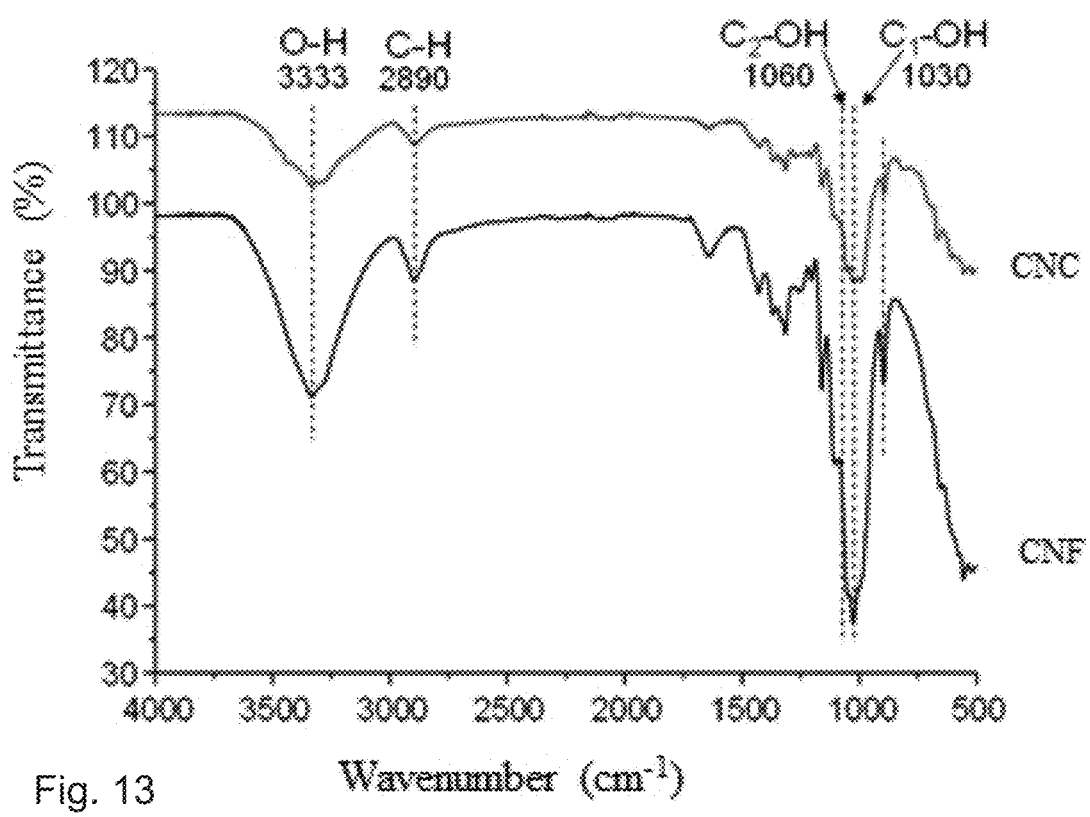
FIG. 13 shows FTIR spectrum of the CNC and CNF

The FTIR spectrum of the CNF and CNC are analyzed and compared, shown in FIG. 13. It can be seen that the CNF and CNC have similar chemical structure (cellulose structure). For example, the absorption peak at 3333 $cm^{-1}$, 2890 $cm^{-1}$, 1060 $cm^{-1}$ and 1030 $cm^{-1}$ was attributed to the O—H stretching, C—H stretching, secondary hydroxyl, primary hydroxyl, respectively. Both the CNF and CNC are prepared from high-purity raw cellulose fibers, therefore they have similar FTIR absorptions.

4.1.4 XRD Analysis of the CNF

Figure 14:
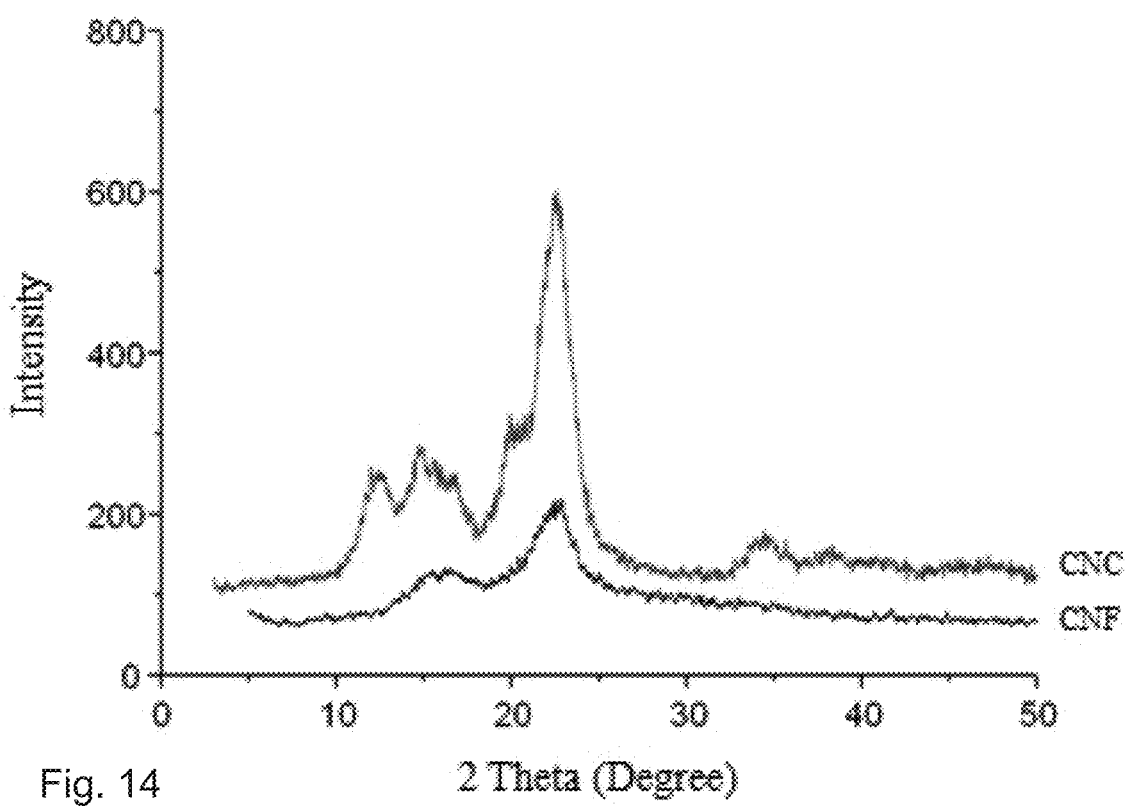
FIG. 14 shows XRD patterns of the CNC and CNF

The XRD patterns of the CNF and CNC were analyzed and compared, shown in FIG. 14. As shown, the weak diffraction peaks of the CNF at 2θ=15.5°, 16.5°, and 22.8° were observed; for comparison, the CNC displayed intense diffraction peaks at 2θ=12.5°, 14.7°, and 22.7°, indicating that the CNC has higher degree of crystallinity than that of the CNF. It was explained that for the CNC, the amorphous region of cellulose was removed through acid hydrolysis and the crystalline region was retained; however, for the CNF, severe mechanical treatment was introduced, including extrusion and tearing, which can severely destroy the crystalline region of the cellulose.

4.2 Concept of Preparing the CNF/AZI Nanocomposite

Figure 4:
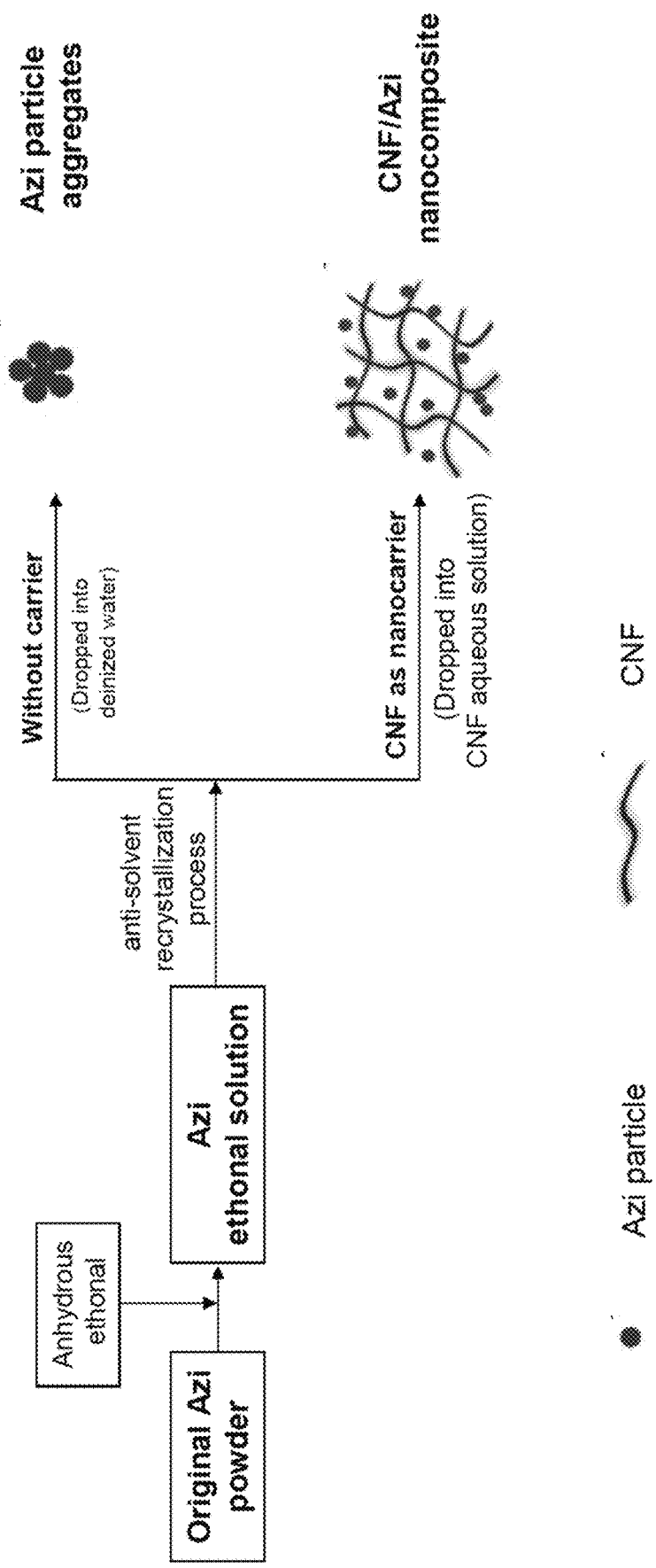
FIG. 4 shows a concept of preparing the CNF/AZI nanocomposites

FIG. 4 shows the concept of preparing the CNF/AZI nanocomposite. In the traditional anti-solvent recrystallization process (upper path), the original AZI is dissolved in solvent (anhydrous ethanol), and then AZI ethanol solution is added dropwise into anti-solvent (deionized water) under different conditions (concentration, volume ratio, temperature and stirring condition)]. With the increase of AZI dosage in deionized water the AZI will reach a supersaturated state and form a lots of AZI nuclei. Due to the hydrophobic nature of AZI, these AZI nuclei will continue to grow, and finally form AZI nanoparticles and aggregates, which are difficult to be further dispersed in aqueous solutions.

When the CNF is used as carrier (lower path), the large specific surface area and the network structure of the CNF will provide more sites for the AZI nuclei, which will prevent the AZI particles from overgrowing and make the AZI nanoparticles more stable in the aqueous solution. The interactions between CNF and AZI could be the electrostatic adsorption and hydrogen bonding.

4.3 Characterization of CNF/AZI Nanocomposite 4.3.1 FTIR Analysis

Figure 15:
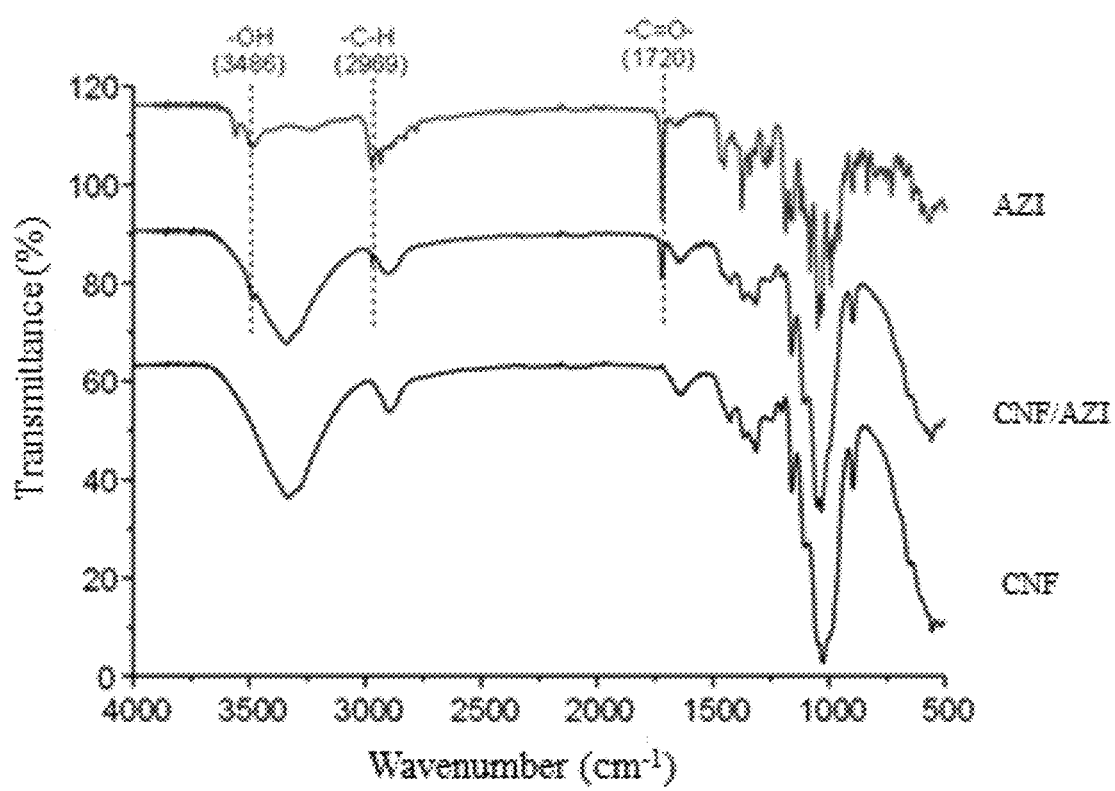
FIG. 15 shows the FTIR spectrum of the CNF, original AZI and CNF/AZI nanocomposite

The FTIR spectrum of original AZI, CNF, and CNF/AZI nanocomposite are shown in FIG. 15. The results showed that original AZI has typical peaks at 3486 cm$^{-1}$, 2969 cm$^{-1}$, and 1720 cm$^{-1}$, representing the O—H stretching, C—H stretching, and C=O stretching, respectively. There are no typical absorption peaks of AZI observed in CNF FTIR results.

For the CNF/AZI nanocomposite, the absorption peaks at 3486 cm$^{-1}$ (O—H stretching), 2969 cm$^{-1}$ (C—H stretching) and 1720 cm$^{-1}$ (C=O stretching) can be observed, which can be attributed to AZI (although the intensity decreased). These results indicated that the AZI was successfully loaded onto the CNF and the chemical structure of AZI had not changed.

4.3.2 XRD Analysis

Figure 16:
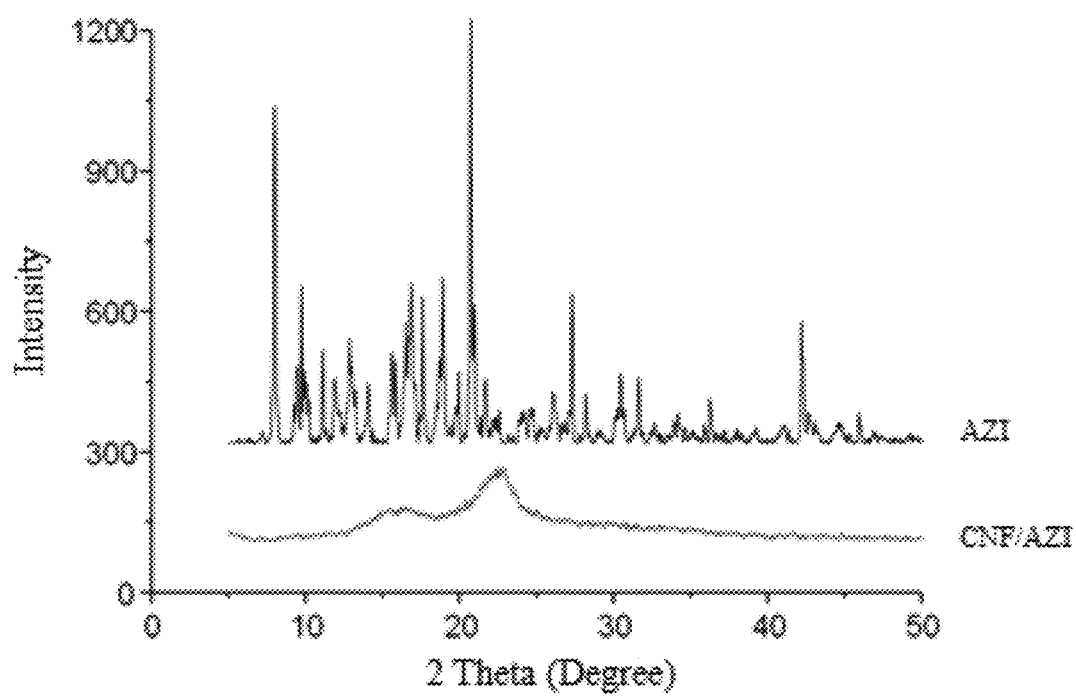
FIG. 16 shows XRD patterns of the AZI and CNF/AZI nanocomposite

The XRD patterns of CNF and CNF/AZI nanocomposite are shown in FIG. 16. The original AZI showed intense diffraction peaks at 2θ=8.0°, 9.8°, 16.9°, 18.9°, 20.7°, 27.3° and 42.3°, indicating that it was in a crystalline state. However, the characteristic diffraction peaks of AZI disappeared in the CNF/AZI nanocomposite, indicating that AZI was transformed from a highly crystalline state to an amorphous state. The nanonization and well dispersion of AZI, based on the formation of CNF/AZI nanocomposite, could be responsible for the transformation of AZI state. The effective nanonization of hydrophobic drugs enhance the water solubility and bioavailability.

4.3.3 TEM Analysis

FIG. 17 shows the TEM images of the original AZI, CNF, and CNF/AZI nanocomposite. The bar is 2 μm in a) and 0.5 μm in b), c) and d). FIG. 17a shows that the original AZI was in a crystalline state and had a large particle size (several micrometers). The AZI particles prepared by the traditional anti-solvent precipitation process were aggregates (FIG. 17b), which were difficult to further disperse in the aqueous solution because of the hydrophobic nature of the AZI.

In contrast, the aggregates of the AZI particles were well dispersed into a number of small and even sized nanoparticles based on the formation of the CNF/AZI nanocomposite (FIG. 17 d), which can be attributed to the electrostatic interaction and hydrogen-bonds interaction between the CNF and AZI particles. The AZI nanoparticles made by the anti-solvent recrystallization process can be easily adsorbed onto the surface of CNF; moreover, the CNF network can help decrease the flocculation of AZI nanoparticles.

4.4 Hydroxyl Radical (OH·) Scavenging Activity of the CNF

Figure 18:
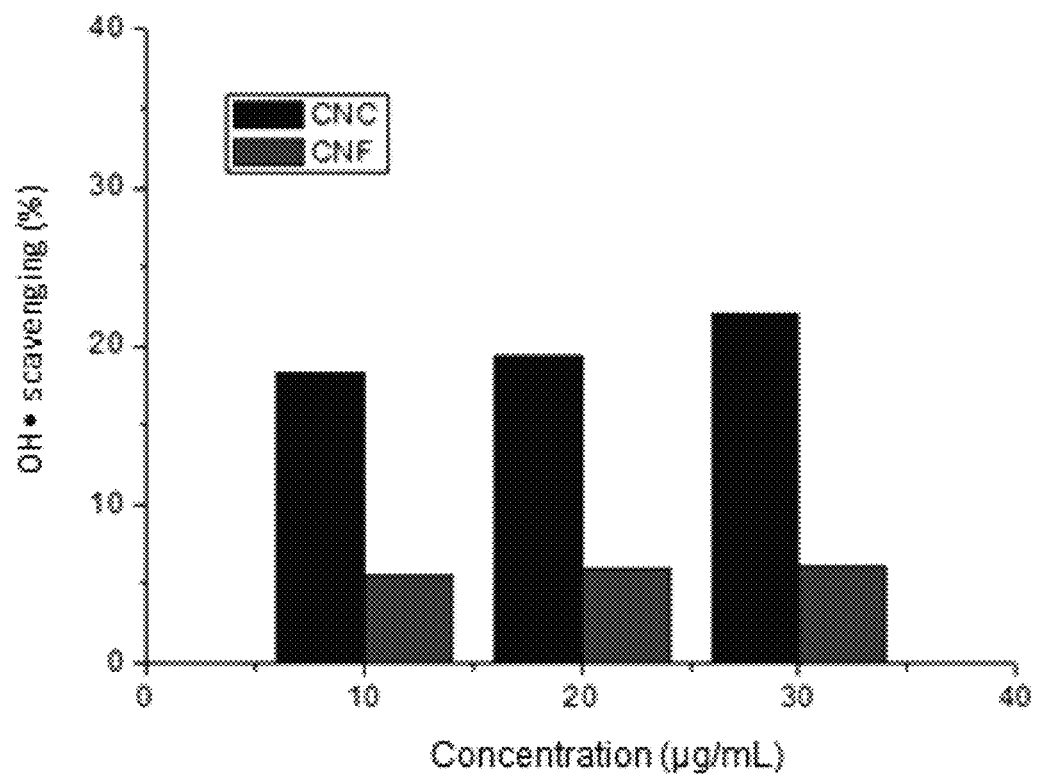
FIG. 18 shows OH· scavenging rates of the CNF and CNC

The previous studies of the present inventors have shown that the CNC has good OH· scavenging activity. Herein, the OH· scavenging activity of the CNF was studied and compared with CNC, shown in FIG. 18.

It can be seen that the CNF has lower OH· scavenging efficiency than that of CNC under the same conditions. For example, the OH· scavenging efficiency of the CNF was in the range of 5.6% to 6.2% under the concentration of 10 to 30 μg/ml; in contrast, the OH· scavenging efficiency of the CNC was in the range of 18.4% to 22.1% under the same concentration.

It was explained that the difference of the amount of cellulose reducing ends resulted in the difference of OH· scavenging efficiency. For the CNF, less cellulose reducing ends were exposed because of its large length and less fiber cross-sections. In contrast, for CNC, a large amount of cellulose reducing ends were exposed because of its small length and more fiber cross-sections.

4.5 In Vitro Dissolution Rate 4.5.1 Standard AZI Curve

Different concentrations of AZI ethanol solution (8-48 μg/ml) were prepared, and the UV absorption at 482 nm was measured for plotting the standard curve of AZI. The Standard curve of AZI was calculated. The equation is as follows: y=22.996x−0.0821, R$^2$=0.9991, indicating that the concentration and absorbance of AZI have a good linear relation.

4.5.2 In Vitro Dissolution Rate of AZI

Figure 19:
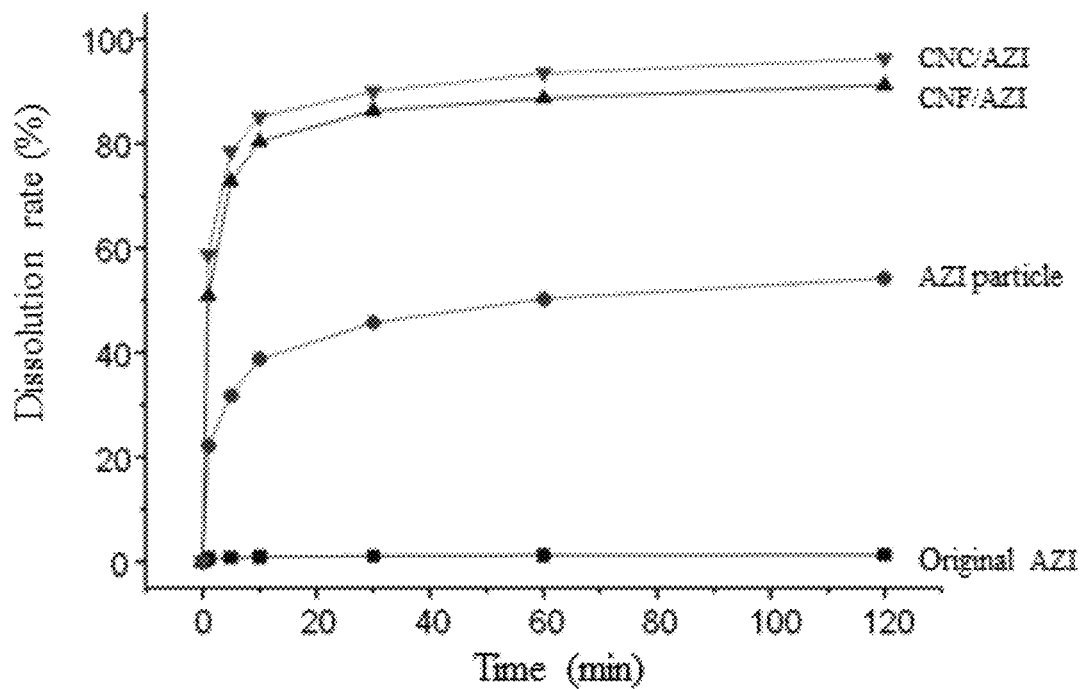
FIG. 19 shows dissolution rate of the original AZI, AZI particle (traditional anti-solvent recrystallization process), CNF/AZI, and CNC/AZI nanocomposites

The dissolution rates of the original AZI, AZI particles (traditional anti-solvent recrystallization process), CNC/AZI, and CNF/AZI nanocomposites are shown in FIG. 19. It can be seen that the original AZI has a very limited dissolution rate, only 1.31% at 120 min. Through anti-solvent recrystallization process, the dissolution rate of AZI increased, and reached 38.8% and 52.2% at 10 min and 120 min, respectively.

In contrast, for the CNF/AZI and CNC/AZI nanocomposites, the dissolution rate of AZI obviously increased. For example, the dissolution rate of AZI in the CNF/AZI and CNC/AZI nanocomposites reached 80.4% and 85.1% at 10 min, respectively; subsequently, the dissolution rate increased slowly and reached 91.2%, and 96.3% at 120 min, respectively. These results indicated that the CNF or CNC as a carrier can effectively enhance the dissolution of AZI.

5. Conclusions 5.1 CNF/AZI nanocomposite was successfully prepared based on the CNF carrier and the anti-solvent recrystallization process. TEM and XRD analyses showed that the AZI was effectively nanonized, well dispersed, and transformed from a highly crystalline state to an amorphous state.

5.2 The OH· scavenging efficiency of the pure CNF (6.2%, 30 μg/ml) is lower than that of the pure CNC (22.1%, 30 μg/ml), which is due to the small amount of cellulose reducing ends in the CNF.

5.3 The dissolution rate of the AZI in the CNF/AZI nanocomposite obviously increased to 91.2% at 120 min, compared with that of the original AZI (1.31%), based on the formation of CNF/Azi nanocomposite.

5.4 The prepared CNF/AZI nanocomposite is promising for enhancing the bioavailability of AZI because of the facile preparation method and good biocompatibility.

The invention claimed is:

1. A method for preparing a pharmaceutical composition, the method comprising:

providing pharmaceutical compound having a solubility in water of 1 mg/ml or less at 25° C. in a solvent comprising an organic solvent enabling solubilizing the pharmaceutical compound at least partly into the solvent, providing an aqueous dispersion of nanostructured cellulose, and adding the pharmaceutical compound in the solvent to the aqueous dispersion of nanostructured cellulose acting as an anti-solvent to obtain a supersaturated concentration of the pharmaceutical compound allowing the pharmaceutical compound to form nuclei at the supersaturated concentration, and then continue to grow by nucleation into nanoparticles in an anti-solvent recrystallization process to provide nanosized pharmaceutical particles having an average diameter of 50 nm or less, to provide a pharmaceutical composition having a water content in the range of 92-99.95% (w/w), wherein the nanostructured cellulose comprises nanofibrillar cellulose which, when dispersed in water, provides a zero shear viscosity in the range of 1000-100000 Pa·s, and a yield stress in the range of 1-50 Pa, determined by rotational rheometer at a consistency of 0.5% (w/w) by weight in aqueous medium at 22° C.±1° C.

2. The method of claim 1, wherein the nanostructured cellulose comprises nanofibrillar cellulose having an average fibril diameter of 200 nm or less.

3. The method of claim 1, wherein the content of nanostructured cellulose in the pharmaceutical composition is in the range of 0.05-8% (w/w).

4. The method of claim 1, wherein the pharmaceutical compound has a solubility in water of 0.6 mg/ml or less at 25° C., and/or low bioavailability.

5. The method of claim 1, wherein the content of the pharmaceutical compound is in the range of 0.05-1 mg, per 100 µl of the pharmaceutical composition.

6. A method for stabilizing a pharmaceutical compound having a low solubility in water of 1 mg/ml or less at 25° C., the method comprising preparing a pharmaceutical composition with the method of claim 1.

7. A method for enhancing bioavailability of a pharmaceutical compound having a low solubility in water of 1 mg/ml or less at 25° C., the method comprising preparing a pharmaceutical composition with the method of claim 1.

8. A pharmaceutical composition prepared in accordance to the method of claim 1, comprising nanosized pharmaceutical particles of a pharmaceutical compound having a solubility in water of 1 mg/ml or less at 25° C., the nanosized pharmaceutical particles having an average diameter of 50 nm or less, in a nanostructured cellulose matrix, the pharmaceutical composition having a water content in the range of 92-99.95% (w/w).

9. The pharmaceutical composition of claim 8, wherein the nanostructured cellulose comprises nanofibrillar cellulose having an average fibril diameter of 200 nm or less.

10. The pharmaceutical composition of claim 9, wherein the nanofibrillar cellulose, when dispersed in water, provides a zero shear viscosity in the range of 1000-100000 Pa·s, and a yield stress (shear stress where the shear thinning begins) in the range of 1-50 Pa, determined by rotational rheometer at a consistency of 0.5% (w/w) by weight in aqueous medium at 22° C.±1° C.

11. The pharmaceutical composition of claim 8, wherein the content of nanostructured cellulose in the pharmaceutical composition is in the range of 0.05-8% (w/w).

12. The pharmaceutical composition of claim 8, wherein the pharmaceutical compound has a solubility in water of 0.6 mg/ml or less at 25° C. and/or low bioavailability.

13. The pharmaceutical composition of claim 8, wherein the content of the pharmaceutical compound is in the range of 0.05-1 mg, per 100 µl of the pharmaceutical composition.

14. The pharmaceutical composition of claim 8, wherein the pharmaceutical compound has a dissolution rate from the nanostructured cellulose matrix of 50% or more in 10 minutes.

15. The pharmaceutical composition of claim 8 obtained with the method of claim 1.

16. The pharmaceutical composition of claim 8 packed into a vial, a capsule or a syringe.

17. A method for treating a subject in need of therapy, the method comprising
recognizing a subject in need of therapy or treatment,
providing the pharmaceutical composition of claim 8, and
delivering or administering the pharmaceutical composition to the subject.

* * * * *